United States Patent
Taniguchi et al.

(10) Patent No.: US 6,265,141 B1
(45) Date of Patent: Jul. 24, 2001

(54) COLOR DEVELOPING AGENT, PROCESSING LIQUID COMPOSITION AND COLOR IMAGE-FORMING METHOD

(75) Inventors: Masato Taniguchi; Kiyoshi Morimoto; Hiroshi Fujimoto; Akimitsu Haijima, all of Minami-Ashigara (JP)

(73) Assignee: Fuji Photo Film Co., Ltd., Minami-Ashigara (JP)

( * ) Notice: Subject to any disclaimer, the term of this patent is extended or adjusted under 35 U.S.C. 154(b) by 0 days.

(21) Appl. No.: 08/275,241

(22) Filed: Jul. 15, 1994

(30) Foreign Application Priority Data

Jul. 24, 1993 (JP) .................................................. 5-202558

(51) Int. Cl.[7] .................................................. G03C 7/413
(52) U.S. Cl. .......................... 430/467; 430/435; 430/484; 430/485
(58) Field of Search .................................. 430/467, 484, 430/485, 435

(56) References Cited

U.S. PATENT DOCUMENTS

| | | | |
|---|---|---|---|
| 3,265,502 | * | 8/1966 | Willems et al. ...................... 430/484 |
| 3,723,117 | * | 3/1973 | Willems ................................ 430/484 |
| 4,113,491 | * | 9/1978 | Deguchi et al. ...................... 430/467 |
| 4,371,609 | * | 2/1983 | Kajiwara et al. ...................... 430/484 |
| 5,328,812 | * | 7/1994 | Haijima et al. ........................ 430/484 |
| 5,344,750 | * | 9/1994 | Fujimoto et al. ..................... 430/484 |

FOREIGN PATENT DOCUMENTS

| | | | |
|---|---|---|---|
| 433812 | * | 6/1991 | (EP) ..................................... 430/467 |
| 97531 | * | 6/1982 | (JP) ..................................... 430/484 |
| 180362 | * | 8/1987 | (JP) ..................................... 430/467 |

* cited by examiner

*Primary Examiner*—Hoa Van Le
(74) *Attorney, Agent, or Firm*—Burns, Doane, Swecker & Mathis, LLP

(57) ABSTRACT

Disclosed are new color developing agents such as those shown below and their analogues:

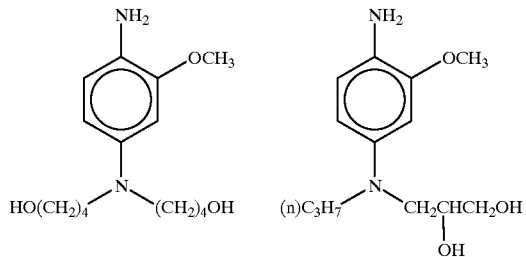

When the color developing agent is used, the color development is accelerated and the developed photosensitive material can be prevented from yellow stain during storage thereof.

9 Claims, No Drawings

COLOR DEVELOPING AGENT, PROCESSING LIQUID COMPOSITION AND COLOR IMAGE-FORMING METHOD

BACKGROUND OF THE INVENTION

The present invention relates to a new silver halide developing agent for color photographs, a processing composition containing the developing agent, and a method for forming a color image with the processing composition. In particular, the present invention relates to a developing agent for color photographs suitable for rapid processing of color photographs and capable of achieving a desired gradation relating to a yellow image, a processing composition containing the developing agent, and a method for forming a color image with the processing composition.

As mini-labs for processing photosensitive materials within the shops and the amount of color negative films used in the field of news photos are increasing recently, the demand for completion of the development process in a shorter time to immediately provide the prints to the customers or to immediately place the photo in newspapers or the like is rapidly increasing. The demand for reduction of the processing time is becoming more and more eager in processing color negative films, since the time necessitated therefor is longer than that necessitated for processing color papers.

For the reduction of the time necessitated for the color development step among the processing steps, Japanese Patent Unexamined Published Application (hereinafter referred to as "J. P. KOKAI") No. Sho 61-261740 discloses a method for processing a color paper mainly comprising a silver chlorobromide emulsion, wherein an N-hydroxyalkyl-substituted p-phenylenediamine derivative is used as the color developing agent; and European Patent No. 410,450 discloses a method for processing a color paper mainly comprising a silver chloride emulsion, wherein a specified N-hydroxyalkyl-substituted p-phenylenediamine derivative is used as the color developing agent. Also, it is disclosed in J. P. KOKAI No. Hei 5-113635 that when 4-(N-ethyl-N-δ-hydroxybutylamino)-2-methylaniline is used in place of ordinarily used 4-(N-ethyl-N-β-hydroxyethylamino)-2-methylaniline in the development of a color photographic sensitive materials mainly comprising a silver bromoiodide emulsion such as color negative films, the sensitivity is unchanged even by reducing the color development time from 3 minute 15 seconds to 2 minute 30 seconds.

Thus the reduction in the processing time is also possible by changing the color developing agent in the color photographic photosensitive materials mainly comprising the silver bromoiodide emulsion such as the color negative films. It was found that the processing time can be remarkably reduced by even only introducing a methoxy group into 2-position to form 4-(N-ethyl-N-δ-hydroxybutylamino)-2-methylaniline as described in the above-described J. P. KOKAI No. Hei 5-113635 or 4-(N-ethyl-N-β-hydroxyethylamino)-2-methoxyaniline as described in J.P. KOKAI No. 53-69035.

However, it was also found that although only magenta and cyan images can be rapidly formed with such a color developing agent, the contract of yellow images becomes seriously low and is practically useless. The problem of the low contrast could not be solved at all with a color developing agent having an alkoxy group at the 2-position such as 4-{N,N-bis(5-hydroxypentylamino)}-2-methoxyaniline described in British Patent No. 807,899, 4-{N,N-bis(5-hydroxypentylamino)}-2-ethoxyaniline described in the above-described J. P. KOKAI No. Hei 5-113635 or 4-(N-butyl-N-β,γ-dihydroxypropylamino)-2-methoxyaniline described in Journal fuer Signalaufzeichungsmaterialien Vol. 2, p. 277 (1974).

Although the color developing agents of the present invention include some of compounds generally set forth in the claim of the above-described British Patent No. 807,899, the specification of this patent has no specific description on the compounds corresponding to the color developing agents of the present invention and there is given no direct description or indirect description suggesting the possibility of reducing the time necessitated for the color developing step and preventing the low contrast of the yellow image at the same time.

SUMMARY OF THE INVENTION

The present invention has been completed under these circumstances. An object of the invention is to provide a color developing agent suitable for use in the rapid processing method and capable of achieving a desired gradation of yellow images; a composition containing the developing agent and used for processing a silver halide color photographic photosensitive material; and a method for forming a color image.

The above-described problem has been solved by: a p-phenylenediamine color developing agent represented by the following general formula (D1) or (D2):

(General Formula D1):

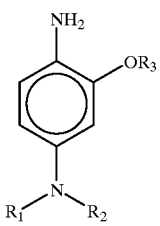

wherein $R_1$ and $R_2$ each represent a hydroxyalkyl group having 2 or more carbon atoms, and $R_1$ represents an alkyl group, with the proviso that the sum of the carbon atoms in $R_1$, $R_2$ and $R_3$ is 9 or below, and (General Formula D2):

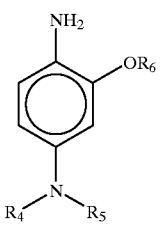

wherein $R_4$ represents an alkyl group having 1 to 3 carbon atoms, $R_5$ represents an alkyl group having at least two hydroxyl groups, and $R_6$ represents an alkyl group having 1 to 4 carbon atoms,

DESCRIPTION OF THE PREFERRED EMBODIMENTS

The detailed description will be made on $R_1$, $R_2$ and $R_3$ in the compounds represented by the general formula (D1) of the present invention.

$R_1$ and $R_2$ each represent a hydroxyalkyl group having 2 or more carbon atoms. $R_1$ and $R_2$ may be the same or different from each other. However, the hydroxyl group may not be bonded to the carbon atom directly bonded to the nitrogen atom. In particular, $R_1$ and $R_2$ each represent a linear, branched or cyclic hydroxyalkyl group having 2 to 6 carbon atoms. The hydroxyl group may be primary, secondary or tertiary hydroxyl group. The hydroxyalkyl group may be further substituted with one or more hydroxyl groups. Examples of them include 2-hydroxyethyl, 3-hydroxypropyl, 3-hydroxycyclopentyl, 2-hydroxypropyl, 4-hydroxybutyl, 5-hydroxypentyl, 2,3-dihydroxypropyl, 6-hydroxyhexyl, 4-hydroxypentyl, 3-hydroxybutyl, 4-hydroxy-4-methylpentyl, 5,6-dihydroxyhexyl, 4-hydroxycyclohexyl, 3,4-dihydroxybutyl, 3-hydroxy-2-(hydroxymethyl) propyl, 2,3,4-trihydroxybutyl, 4-hydroxy-3-(hydroxymethyl)butyl and 2-hydroxy-2-methylpropyl groups. Each of $R_1$ and $R_2$ is preferably a linear or branched hydroxyalkyl group. It is preferred that at least one of $R_1$ and $R_2$ is a primary hydroxyalkyl group. The sum of the hydroxyl groups in $R_1$ and $R_2$ is preferably 4 or below, more preferably 3 or below and most preferably 2.

$R_3$ is an alkyl group having 1 to 5 carbon atoms. In particular, $R_3$ is an a linear, branched or cyclic alkyl group having 1 to 5 carbon atoms such as methyl, ethyl, n-propyl, isopropyl, n-butyl, sec-butyl, ti-butyl, neopentyl or cyclopropyl group. $R_3$ has preferably 1 to 3 carbon atoms.

The sum of carbon atoms in $R_1$, $R_2$ and $R_3$ is 9 or below. It is preferred that the sum of them is 6 to 9. More preferably, $R_3$ is methyl or ethyl group and the sum of the carbon atoms in $R_1$, $R_2$ and $R_3$ is 6 to 9. Most preferably, the sum of them is 7 or 8, or the compound is compound (D-11) given below.

The detailed description will be made on $R_4$, $R_5$ and $R_6$ in the compounds represented by the general formula (D2) in the present invention.

$R_4$ is an alkyl group having 1 to 3 carbon atoms. In particular, $R_4$ is methyl, ethyl, n-proyl, isopropyl or cyclopropyl group.

$R_5$ is an alkyl group having at least two hydroxyl groups, with the proviso that the hydroxyl groups cannot be bonded to the carbon atom directly bonded to the nitrogen atom. In particular, $R_5$ is a linear, branched or cyclic alkyl group having at least two hydroxyl groups and 3 to 9 carbon atoms, preferably 3 to 7 carbon atoms. The hydroxyl group may be primary, secondary or tertiary. Examples of them include 3,4-dihydroxybutyl, 4,5-dihydroxypentyl, 2,3-dihydroxypropyl, 2,4-dihydroxybutyl, 5,6-dihydroxyhexyl, 6,7-dihydroxyheptyl, 3,4-dihydroxycyclohexyl, 3-hydroxy-2-(hydroxymethyl)propyl, 2,3,4-trihydroxybutyl, 3,4,5-trihydroxypentyl, 4-hydroxy-3-(hydroxymethyl) butyl, 2,3-dihydroxy-2-methylpropyl, 3,4-dihydroxy-2-methylbutyl, 2,3,4,5,6-pentahydroxyhexyl, 3,4,5-trihydroxypentyl, 2,3,4,5-tetrahydroxypentyl and 2,3-dihydroxybutyl groups.

$R_5$ is preferably a linear or branched alkyl group, more preferably a linear alkyl group. $R_5$ has preferably 3 or less hydroxyl groups, more preferably 2 hydroxyl groups.

$R_6$ is an alkyl group having 1 to 4 carbon atoms. In particular, $R_6$ is methyl, ethyl, n-propyl, isopropyl, n-butyl, sec-butyl or t-butyl group.

The sum of carbon atoms in $R_4$, $R_5$ and $R_6$ is preferably 5 to 10, more preferably 5 to 9. More preferably, $R_6$ is methyl or ethyl group and the sum of the carbon atoms in $R_4$, $R_5$ and $R_6$ is 5 to 9. Most preferably, the sum of them is 6 or 7.

Examples of typical developing agents represented by the general formulae (D1) and (D2) in the present invention will be given below, which by no means limit the invention.

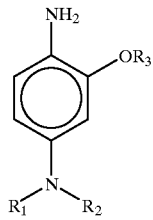

(D1)

| Compound No. | $R_1$ | $R_2$ | $R_3$ |
|---|---|---|---|
| D-1 | -(CH$_2$)$_3$-OH | -(CH$_2$)$_3$-OH | —CH$_3$ |
| D-2 | -(CH$_2$)$_2$-OH | -(CH$_2$)$_4$-OH | —CH$_3$ |
| D-3 | -(CH$_2$)$_2$-OH | -(CH$_2$)$_4$-OH | —C$_2$H$_5$ |
| D-4 | —CH$_2$CH(OH)—CHCH$_2$OH(OH) | -(CH$_2$)$_3$-OH | —CH$_3$ |

-continued

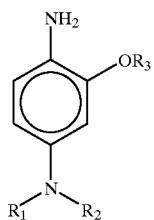

(D1)

| Compound No. | R₁ | R₂ | R₃ |
|---|---|---|---|
| D-5 | —CH₂CH(OH)—CHCH₃(OH) | —(CH₂)₃—OH | —C₂H₅ |
| D-6 | —(CH₂)₂—OH | —(CH₂)₃—OH | —C₃H₇ (i) |
| D-7 | —(CH₂)₄—OH | —(CH₂)₃—OH | —CH₃ |
| D-8 | —(CH₂)₂—OH | —(CH₂)₂—OH | —C₅H₁₁ (n) |
| D-9 | —(CH₂)₂—CHCH₂OH(OH) | —(CH₂)₂—OH | —C₃H₇ (n) |
| D-10 | —(CH₂)₂—OH | —CH₂CHCH₃(OH) | —C₄H₉ (t) |
| D-11 | —(CH₂)₄—OH | —(CH₂)₄—OH | —CH₃ |
| D-12 | —CH₂CHCH₂CH₂OH(OH) | —(CH₂)₃—OH | —C₂H₅ |
| D-13 | —(CH₂)₂—OH | —(CH₂)₃—OH | —CH₃ |
| D-14 | —CHCH₂OH(CH₂OH) | —(CH₂)₂—OH | —C₄H₉ (n) |
| D-15 | —(CH₂)₃—OH | —(CH₂)₃—OH | —C₂H₅ |
| D-16 | (4-methylcyclohexane-1,2-diol group) | —(CH₂)₂—OH | —CH₃ |
| D-17 | —(CH₂)₂—OH | —(CH₂)₃—OH | —C₂H₅ |
| D-18 | —CH₂C(CH₃)(CH₃)(OH) | —(CH₂)₂—CHCH₂OH(OH) | —CH₃ |
| D-19 | —(CH₂)₂—OH | —(CH₂)₂—OH | —CH₃ |
| D-20 | —(CH₂)₂—CHCH₃(OH) | —(CH₂)₃—OH | —CH₃ |
| D-21 | —(CH₂)₂—OH | —(CH₂)₂—OH | —C₂H₅ |
| D-22 | —(CH₂)₂—CHCH₂OH(CH₃) | —(CH₂)₃—OH | —CH₃ |
| D-23 | —(CH₂)₆—OH | —(CH₂)₂—OH | —CH₃ |

-continued

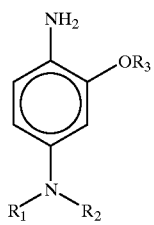

(D1)

| Compound No. | $R_1$ | $R_2$ | $R_3$ |
|---|---|---|---|
| D-24 | —(CH$_2$)$_2$—OH | —(CH$_2$)$_2$—OH | —C$_3$H$_7$ (i) |

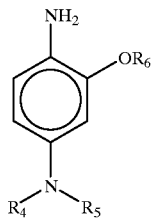

(D2)

| Compound No. | $R_4$ | $R_5$ | $R_6$ |
|---|---|---|---|
| D-25 | —C$_3$H$_7$ (n) | —CH$_2$CHCH$_2$OH<br>      \|<br>      OH | —CH$_3$ |
| D-26 | —C$_2$H$_5$ | —CH$_2$CH$_2$CHCH$_2$OH<br>          \|<br>          OH | —CH$_3$ |
| D-27 | —CH$_3$ | —CH$_2$CH$_2$CH—CHCH$_2$OH<br>         \|     \|<br>         OH  OH | —C$_3$H$_7$ (n) |
| D-28 | —C$_2$H$_5$ | —CH$_2$CHCH$_2$CH$_2$OH<br>      \|<br>      OH | —CH$_3$ |
| D-29 | —CH$_3$ | —CH$_2$CH$_2$CHCH$_2$OH<br>        \|<br>        OH | —C$_2$H$_5$ |
| D-30 | —C$_2$H$_5$ | —CH$_2$CHCH$_2$OH<br>      \|<br>      OH | —CH$_3$ |
| D-31 | —CH$_3$ | —CH$_2$CHCH$_2$OH<br>      \|<br>      OH | —CH$_3$ |
| D-32 | C$_3$H$_7$ (n) | —CH$_2$CHCH$_2$CH$_2$OH<br>      \|<br>      OH | —CH$_3$ |
| D-33 | —CH$_3$ | —CH$_2$CH—CHCH$_3$<br>      \|     \|<br>      OH  OH | —C$_3$H$_7$ (i) |

-continued

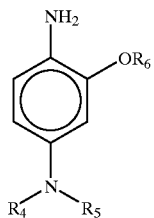
(D2)

| Compound No. | $R_4$ | $R_5$ | $R_6$ |
|---|---|---|---|
| D-34 | —$CH_3$ | —$CH_2CH_2CHCH_2OH$ with OH on the CH | —$C_4H_9$ (t) |
| D-35 | —$CH_3$ | —$CH_2CH_2CHCH_2OH$ with OH on the CH | —$CH_3$ |
| D-36 | —$CH_3$ | —CH(CH$_2$OH)(CH$_2$OH) | —$CH_3$ |
| D-37 | —$C_2H_5$ | —$CH_2CH$—$CH$—$CHCH_2OH$ with OH, OH, OH | —$C_2H_5$ |
| D-38 | —$C_3H_7$ (n) | —$CH_2CH$—$CHCH_2OH$ with $CH_3$, OH | —$C_2H_5$ |
| D-39 | —$C_2H_5$ | —$CH_2C(CH_3)(OH)$—$CH_2OH$ | —$C_3H_7$ (n) |
| D-40 | —$C_2H_5$ | —$CH_2CHCH_2CH_2OH$ with OH | —$CH_3$ |
| D-41 | —$C_2H_5$ | —$CH_2CH_2CHCH_2CH_2OH$ with OH | —$CH_3$ |
| D-42 | —$C_3H_7$ (n) | —$(CH_2)_4$—$CHCH_2OH$ with OH | —$CH_3$ |
| D-43 | —$CH_3$ | —$(CH_2)_5$—$CHCH_2OH$ with OH | —$C_4H_9$ (n) |
| D-44 | —$CH_3$ | cyclohexyl with two OH groups | —$C_4H_9$ (t) |

Among the above-mentioned compounds of the general formula (D1), preferred are (D-1), (D-2), (D-3), (D-7); (D-11) and (D-17).

Since the compounds of the general formulae (D1) and (D2) are very unstable when they are stored in the form of the free amines, they are usually stored in the form of salts with an inorganic or organic acid, and converted into the free amines when they are to be added to the processing solution. Examples of the inorganic and organic acids usable for converting the compounds of the general formulae (D1) and (D2) into their salts include hydrochloric acid, sulfuric acid, phosphoric acid, p-toluenesulfonic acid, methanesulfonic acid and naphthalene-1,5-disulfonic acid. Among them, the sulfates and p-toluenesulfonates are preferred, and particularly the sulfates are most preferred.

The processing composition of the present invention is a solution containing a color developing agent of the general formula (D1) or (D2). It may be a developer per se or a concentrate thereof.

The color developing agent of the present invention is used in an amount of preferably 0.3 to 100 mmol, more preferably 3 to 90 mmol, per liter of the developer.

The processing temperature for the developer is 20 to 60° C., preferably 30 to 55° C. In this connection, it is preferable that the develping be carried out for 15 seconds to 3 minutes and 15 seconds, more preferably 30 seconds to 2 minutes and 30 seconds, although the developing is generally carried out for 10 seconds to 10 minutes. The developing agent of the present invention is useful in particular for preventing soft degradation of yellow images particularly appearing in cases where the time period for the color developing is set at 3 minutes and 15 seconds or less.

The color developing agent of the present invention can be easily synthesized by, for example, a method described in Journal of the American Chemical Society, Vol. 73, p. 3100 (1951) and British Patent No. 807,899. Further, a method given in the following Synthesis Example or the like can also be employed. Synthesis Example Compound (D-1) of the present invention as mentioned above was synthesized according to the following scheme:

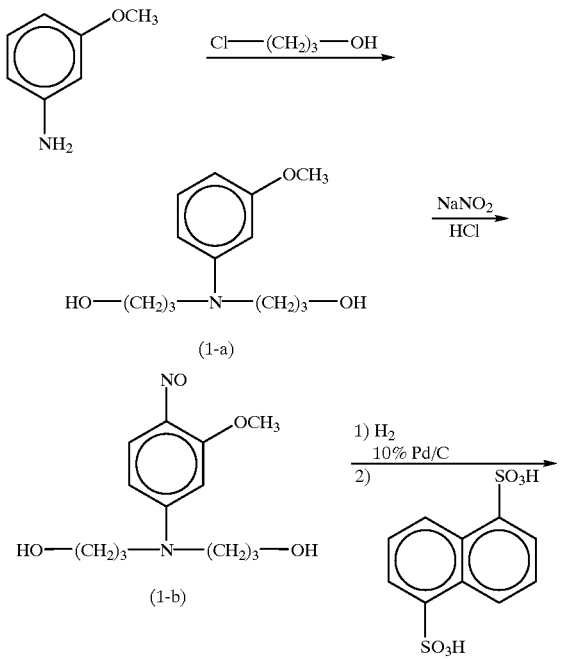
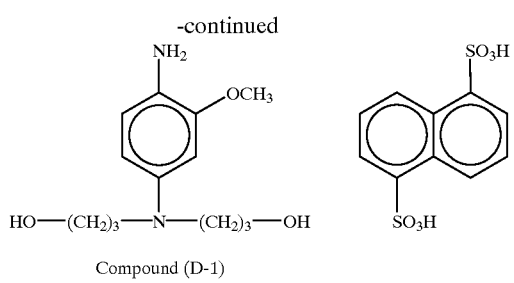

Compound (D-1)

Synthesis of Compound (1-a):
20 g of m-anisidine, 34.2 g of sodium hydrogencarbonate and 9.7 g of sodium iodide were added to 80 ml of dimethylacetamide. 38.4 g of 3-chloro-1-propanol was added to the resultant mixture under stirring at 120° C. for 1 hour. The mixture thus obtained was heated under stirring for additional 4 hours. After leaving the mixture to cool, it was poured into water. After extraction from ethyl acetate followed by washing with watr and concentration, the product was purified by silica gel column chromatography to obtain 35 g of Compound (1-a) in the form of a yellow oily substance.

Synthesis of Compound (1-b):
43.4 g of Compound (1-a) was added to a mixed solution of 200 ml of water and 33.3 g of concentrated hydrochloric acid. A solution of 11.9 g of sodium nitrite in 50 ml of water was added to the resultant mixture for 30 min while the internal temperature was kept at 5° C. The mixture was stirred at room temperature for additional one hour. 18.3 g of sodium hydrogencarbonate was added to the mixture. The reaction mixture was concentrated. After removing the inorganic matter by filtration, the product was purified by silica gel column chromatography to obtain 40 g of Compound (1-b) in the form of a green oily substance.

Synthesis of Compound (D-1) Mentioned Above:
40 g of Compound (1-b) and 0.5 g of 10% palladium/carbon were added to 200 ml of methanol, and the resultant mixture was stirred in an autoclave at an internal temperature of 40° C. under hydrogen pressure of 50 kg/cm$^2$ for 2 hours. The catalyst was removed by filtration, and the filtrate was added dropwise to a solution of 53.7 g of 1,5-naphthalenedisulfonic acid tetrahydrate in methanol. The crystals thus formed were taken by filtration to obtain 65.5 g of 1,5naphthalenedisulfonate of the intended compound (D-1) in the form of colorless crystals. Melting point: 262° C. (decomposition). Elementary analysis for $C_{23}H_{30}N_2O_9S_2$ (%)

|  | C | H | N | S |
|---|---|---|---|---|
| Calculated: | 50.86 | 5.53 | 5.16 | 11.79 |
| Found: | 50.60 | 5.55 | 5.01 | 11.63 |

The color developing agent of the present invention can be used either singly or in combination with other known p-phenylenediamine derivatives. Typical examples of the compounds which can be used in combination with the color developing agent include the following compounds, which by no means limit them:

P-1: N,N-diethyl-p-phenylenediamine,
P-2: 2-amino-5-(N,N-diethylamino)toluene,
P-3: 2-amino-5-(N-ethyl-N-laurylamino)toluene,
P-4: 4-[N-ethyl-N-(β-hydroxyethyl)amino]aniline,
P-5: 2-methyl-4-[N-ethyl-N-(β-hydroxyethyl)amino]aniline,
P-6: 4-amino-3-methyl-N-ethyl-N-[β-(methanesulfonamido)ethyl]aniline,
P-7: N-(2-amino-5-N,N-diethylaminophenylethyl)methanesulfonamide,
P-8: N,N-dimethyl-p-phenylenediamine,
P-9: 4-amino-3-methyl-N-ethyl-N-methoxyethylaniline,
P-10: 4-amino-3-methyl-N-ethyl-N-β-ethoxyethylaniline,
P-11: 4-amino-3-methyl-N-ethyl-N-β-butoxyethylaniline.

Among the above-described p-phenylenediamine derivatives to be used for the combination, particularly preferred are compounds P-5 and P-6. The p-phenylenediamine derivatives are usually used in the form of their salts such as sulfates, hydrochlorides, sulfites, p-toluenesulfonates, nitrates and naphthalene-1,5-disulfonates. The aromatic primary amine developing agent is used in an amount of preferably about 0.3 to 70 mmol per liter of the developer. The amount of the developing agent used in combination of the developing agent of the present invention is preferably ⅟₁₀ to 10 mol, per mol of the developing agent of the present invention represented by the above general formula so far as the effect of the invention is not impaired.

The color developer used in the present invention is usually alkaline. It is preferably an alkaline aqueous solution having a pH of 9 to 12.5.

When the color developing agent of the present invention is incorporated into the color photosensitive material, it can be preferably incorporated into an emulsion layer in the form of a precursor. In such a case, it is used in an amount of preferably about 0.2 to 20 $mmol/ml^2$.

At least one layer among a blue-sensitive layer, a green-sensitive layer and a red-sensitive layer comprising a silver halide emulsion is formed on a support to form a photosensitive material used in the present invention. The number or the order of the arrangement of the silver halide emulsion layer(s) and the photoinsensitive layer(s) is not particularly limited. A typical example of the silver halide photosensitive material comprises at least one photosensitive layer (comprising two or more silver halide emulsion layers having substantially the same color sensitivity but different degree of sensitivity) formed on the support. The photosensitive layer is a unit photosensitive layer sensitive to any of blue, green and red lights. In the multi-layered silver halide color photosensitive materials, the arrangement of the unit photosensitive layers is as follows: a red-sensitive layer, a green-sensitive layer and a blue-sensitive layer in this order from the support. However, the order may be reversed or a sensitive layer may be interposed between two layers sensitive to another color depending on the purpose.

A photoinsensitive layer such as an intermediate layer can be provided between the silver halide photosensitive layers or as the top layer or the bottom layer.

The intermediate layer may contain a coupler or DIR compound as described in J.P. KOKAI Nos. Sho 61-43748, Sho 59-113438, Sho 59-113440,, Sho 61-20037 and Sho 61-20038, or an ordinary color-mixing inhibitor.

The two or more silver halide emulsion layers constituting the unit photosensitive layer have preferably a structure consisting of two layers, i.e. a high sensitivity emulsion layer and a low sensitivity emulsion layer, as described in West German Patent No. 1,121,470 or British Patent No. 923,045. Usually the arrangement of the layers is such that the sensitivity thereof decreases gradually toward the support. A photoinsensitive layer may be provided between the silver halide emulsion layers. An emulsion layer having a low sensitivity may be formed away from the support and an emulsion layer having a high sensitivity may be formed close to the support as described in J.P. KOKAI Nos. Sho 57-112751, Sho 62-200350, Sho 62-206541 and Sho 62-206543.

An example of the arrangement is a structure of a blue-sensitive layer having a low sensitivity (BL)/blue-sensitive layer having a high sensitivity (BH)/green-sensitive layer having a high sensitivity (GH)/green-sensitive layer having a low sensitivity (GL)/red-sensitive layer having a high sensitivity (RH)/red-sensitive layer having a low sensitivity (RL); BH/BL/GL/GH/RH/RL; or BH/BL/GH/GL/RL/RH toward the support.

As described in J.P. KOKOKU No. Sho 55-34932, the arrangement may be a blue-sensitive layer/GH/RH/GL/RL toward the support. Another arrangement is a blue-sensitive layer/GL/RL/GH/RH toward the support as described in J.P. KOKAI Nos. Sho 56-25738 and Sho 62-63936.

Another arrangement is that of three layers having sensitivities gradually lowered toward the support, i.e. a top layer (a silver halide emulsion layer having the highest sensitivity), middle layer (a silver halide emulsion layer having a lower sensitivity) and bottom layer (a silver halide emulsion layer having a sensitivity lower than that of the middle layer) as described in J.P. KOKOKU No. 49-15495. Even in such an arrangement, sensitive layers having the same-color sensitivity may comprise further an emulsion layer having a medium sensitivity/emulsion layer having a high sensitivity/emulsion layer having a low sensitivity in the order toward the support as described in J.P. KOKAI No. 59-202464.

In another example, the arrangement is as follows: high-sensitivity emulsion layer/low sensitivity emulsion layer/medium sensitivity emulsion layer or low sensitivity emulsion layer/medium sensitivity emulsion layer/high sensitivity emulsion layer. When the photosensitive material has four or more layers, the arrangement of them may be varied as described above.

To improve the color reproducibility, it is preferred to arrange a donor layer (CL) having an interlayer effect and a spectral sensitivity distribution different from that of the main photosensitive layer such as BL, GL or RL adjacent to or close to the main photosensitive layer as described in U.S. Pat. Nos. 4,663,271, 4,705,744 and 4,707,436 and J.P. KOKAI Nos. Sho 62-160448 and Sho 63-89850.

As described above, the layer structure and arrangement can be selected from various ones depending on the use of the photosensitive material.

When the photosensitive material used in the present invention is a color negative film or a color reversal film, the preferred silver halide to be contained in the photographic emulsion layer is silver bromoiodide, silver chloroiodide or silver chlorobromoiodide containing about 30 molar % or below of silver iodide. Particularly preferred is silver bromoiodide or silver chlorobromoiodide containing about 2 to 25 molar % of silver iodide, since rapid processing of high level can be achieved by use of the color developing agent of the present invention.

When the photosensitive material used in the present invention is a direct positive color photosensitive material, the preferred silver halide to be contained in the photographic emulsion layer thereof is silver chlorobromide or silver bromide.

When the photosensitive material used in the present invention is a color photographic paper, the preferred silver halide to be contained in the photographic emulsion layer thereof is silver chlorobromide or silver chloride substantially free from silver iodide. The term "substantially free from silver iodide" herein indicates that the silver iodide content is 1 molar % or below, preferably 0.2 molar % or below. In the halogen composition of the silver chlorobromide emulsion, the ratio of silver bromide to silver chloride is selected in a wide range depending on the purpose. Particularly, a silver chloride content of at least 2 molar % is preferred. For the photosensitive material suitable for the rapid process, a so-called high silver chloride emulsion having a high silver chloride content is preferred. The silver chloride content of the high-silver chloride emulsion is preferably at least 90 molar %, more preferably at least 95 molar %. A silver chlorobromide emulsion wherein the silver chlorobromide comprises substantially pure silver chloride (i.e. silver chloride content of 98 to 99.9 molar %) is also preferred.

The silver halide grains in the photographic emulsion may be in a regular crystal form such as a cubic, octahedral or tetradecahedral form; an irregular crystal form such as spherical or plate form; or a complex crystal form thereof. They include also those having a crystal fault such as a twin plate.

The silver halide grain diameter may range from about 0.2 μm or less to as large as that having a projection area diameter of about 10 μm. The emulsion may be either a polydisperse emulsion or monodisperse emulsion.

The silver halide photographic emulsion usable in the present invention can be prepared by processes described in, for example, Research Disclosure (RD), No. 17643 (December, 1978), pp. 22 to 23, "1. Emulsion preparation and types"; RD No. 18716 (November, 1979), p. 648; RD No. 307105 (November, 1989), pp. 863 to 865; P. Glafkides, Chemie et Phisique Photographique, Paul Montel, 1967; G. F. Duffin, Photographic Emulsion Chemistry (Focal Press, 1966); V. L. Zelikman et al., Making and Coating Photographic Emulsion (Focal Press, 1964).

Monodisperse emulsions described in U.S. Pat. Nos. 3,574,628 and 3,655,394 and British Patent No. 1,413,748 are also preferred.

Tabular grains having an aspect ratio of 3 or higher are also usable. The tabular grains can be easily prepared by processes described in, for example, Gutoff, Photographic Science and Engineering, Vol. 14, pp. 248 to 257 (1970); U.S. Pat. Nos. 4,434,226, 4,414,310, 4,433,048 and 4,439,520; and British Patent No. 2,112,157.

The crystal structure of the grains in the above emulsion may be uniform; the grains may comprise an inside protion and an outside portion which are composed of silver halides different from each other; or the structure may be a laminated one. Different silver halide grains can be bonded together by an epitaxial bond or they can be bonded with a compound other than silver halides such as silver rhodanate or lead oxide. A mixture of grains having various crystal forms can also be used.

The emulsion may be of a surface-latent image type for forming a latent image mainly on the surface thereof, of an internal latent image type for forming a latent image in the grains or of such a type that a latent image is formed both on the surface and in the grains. The emulsion must be a negative one. In the internal latent image type emulsions, a core/shell type internal latent image type emulsion described in J.P. KOKAI No. Sho 63-264740 may also be used. Processes for producing the core/shell type internal latent image type emulsion are described in J.P. KOKAI No. Sho 59-133542. The thickness of the shells in the emulsion which varies depending on the developing process is preferably 3 to 40 nm, particularly preferably 5 to 20 nm.

The silver halide emulsion to be used in the present invention is usually physically and chemically ripened and spectrally sensitized. The additives to be used in these steps are shown in Research Disclosure Nos. 17643, 18716 and 307105. The portions in which the additives are mentioned in these three Research Disclosures are summarized in a table given below.

A mixture of two or more photosensitive silver halide emulsions, different from one another in at least one of grain size, grain size distribution, halogen components, shape of the grains and sensitivity can be used for forming a layer.

Silver halide grains having the fogged surface described in U.S. Pat. No. 4,082,553, silver halide grains having fogged core and colloidal silver described in U.S. Pat. No. 4,626,498 and J.P. KOKAI No. Sho 59-214852 can be preferably used for forming the photosensitive silver halide emulsion layer and/or substantially photo-insensitive, hydrophilic colloid layer. The term "&silver halide grains having fogged core or surface" indicates silver halide grains which can be subjected to uniform (non-imagewise) development irrespective of exposed or non-exposed parts of the photosensitive material. Processes for producing the silver halide grains having the fogged core or surface are described in U.S. Pat. No. 4,626,498 and J.P. KOKAI No. 59-214852.

The silver halide for forming the core of the core/shell type silver halide grains having the fogged core may have the same or different halogen composition. The silver halides having the fogged core or surface include silver chloride, silver chlorobromide, silver bromoiodide and silver chlorobromoiodide. Although the size of the fogged silver halide grains is not particularly limited, the average grain size thereof is preferably 0.01 to 0.75 μm, particularly 0.05 to 0.6 μm. The shape of the grains is not particularly limited. The grains may be regular or in the form of a polydisperse emulsion. The dispersion is preferably of monodisperse system wherein at least 95% (by weight or by number of the grains) of the silver halide grains have a grain diameter within the average grain diameter ±40%.

Fine grains of a photo-insensitive silver halide are preferably used in the present invention. The term "fine grains of photo-insensitive silver halide" indicates fine silver halide grains which are not sensitized in the image-forming exposure for forming a dye image and which are substantially not developed in the developing process. They are preferably previously not fogged.

The fine silver halide grains have a silver bromide content of 0 to 100 molar %. If necessary, they may contain silver chloride and/or silver iodide. They preferably contain 0.5 to 10 molar % of silver iodide.

The fine silver halide grains have an average grain diameter (average diameter of a projected area) of preferably 0.01 to 0.5 μm, more preferably 0.02 to 0.2 μm.

The fine silver halide grains can be prepared by the same processes as those for the productin of ordinary photosensitive silver halides. In this case, it is unnecessary to chemically sensitize or spectrally sensitize the surface of the silver halide grains. It is preferred, however, to incorporate a known stabilizer such as a triazole, azaindene, benzothiazolium or mercapto compound or a zinc compound thereinto prior to the incorporation thereof into a coating solution. Colloidal silica can be preferably incorporated into the fine silver halide grain-containing layer.

The amount of silver to be applied to the photosensitive material used in the present invention is preferably not larger than 6.0 g/m², most preferably not larger than 4.5 g/m².

Known photographic additives usable in the present invention are also mentioned in the three Research Disclosures, and the corresponding portions are also shown in the following table.

| Additive | RD 17643 | RD 18716 | RD 307105 |
|---|---|---|---|
| 1. Chemical sensitizer | p. 23 | p. 648, right column | p. 866 |
| 2. Sensitivity improver | | ditto | |
| 3. Spectral sensitizer and supersensitizer | pp. 23 to 24 | p. 648, right column to p. 649, right column | pp. 866 to 868 |
| 4. Brightening agent | p. 24 | p. 647, right column | p. 868 |
| 5. Antifoggant and stabilizer | pp. 24 and 25 | p. 649, right column | pp. 868 to 870 |
| 6. Liqht absorber, filter, dye and UV absorber | pp. 25 to 26 | p. 649, riqht column to p. 650, left column | p. 873 |
| 7. Antistaining agent | p. 25, right column | p. 650, left and right columns | p. 872 |
| 8. Dye imaqe stabilizer | p. 25 | p. 650, left column | ditto |
| 9. Hardener | p. 26 column | p. 651, left | pp. 874 to 875 |
| 10. Binder | ditto | ditto | pp. 873 to 874 |
| 11. Plasticizer and lubricant | p. 27 | p. 650, right column | p. 876 |
| 12. Coating aid and surfactant | pp. 26 and 27 | ditto | pp. 875 to 876 |
| 13. Antistatic agent | p. 27 | ditto | pp. 876 to 877 |
| 14. Matting agent | | | pp. 878 to 879 |

To prevent the deterioration of the photographic properties by gaseous formaldehyde, it is preferred to add to the photosensitive material a compound capable of reacting with formaldehyde to fix it as described in U.S. Pat. Nos. 4,411,987 and 4,435,503.

It is preferred to incorporate a mercapto compound described in U.S. Pat. Nos. 4,740,454 and 4,788,132, J.P. KOKAI Nos. Sho 62-18539 and Hei 1-283551 into the photosensitive material of the present invention.

It is also preferred to incorporate a fogging agent, development accelerator, solvent for the silver halides or a precursor thereof into the photosensitive material of the present invention irrespective of the amount of the developing silver formed by the development which is described in J.P. KOKAI No. Hei 1-106052.

It is also preferred to incorporate a dye dispersed by a process described in International Publication No. WO 88/04794 and J.P.Kokai No. Hei 1-502912 or a dye described in EP 317,308A, U.S. Pat. No. 4,420,555 and J.P. KOKAI No. Hei 1-259358.

Various color couplers can be used in the present invention. Examples of them are given in patents described in the above-described Research Disclosure No. 17643, VII-C to G and No. 307105, VII-C to G.

Preferred yellow couplers are those described in, for example, U.S. Pat. Nos. 3,933,051, 4,022,620, 4,326,024, 4,401,752 and 4,248,961, J.P. KOKOKU No. Sho 58-10739, British Patent Nos. 1,425,020 and 1,476,760, U.S. Pat. Nos. 3,973,968, 4,314,023 and 4,511,649, and European Patent No. 249,473A.

Particularly preferred magenta couplers are 5-pyrazolone and pyrazoloazole compounds. Particularly preferred are those described in U.S. Pat. Nos. 4,310,619 and 4,351,897, European Patent No. 73,636, U.S. Pat. Nos. 3,061,432 and 3,725,067, Research Disclosure No. 24220 (June, 1984), J.P. KOKAI No. Sho 60-33552, Research Disclosure No. 24230 (June, 1984), J.P. KOKAI Nos. Sho 60-43659, Sho 61-72238, Sho 60-35730, Sho 55-118034 and Sho 60-185951, U.S. Pat. No. 4,500,630, 4,540,654 and 4,556, 630, and International Publication No. WO 88/04795.

The cyan couplers usable in the present invention are phenolic and naphtholic couplers. Particularly preferred are those described in U.S. Pat. Nos. 4,052,212, 4,146,396, 4,228,233, 4,296,200, 2,369,929, 2,801,171, 2,772,162, 2,895,826, 3,772,002, 3,758,308, 4,334,011 and 4,327,173, West German Patent Unexamined Published Application No. 3,329,729, European Patent Nos. 121,365A and 249, 453A, U.S. Pat. Nos. 3,446,622, 4,333,999, 4,775,616, 4,451,559, 4,427,767, 4,690,889, 4,254,212 and 4,296,199, and J.P. KOKAI No. Sho 61-42658. Further, pyrazoloazole couplers described in J.P. KOKAI Nos. Sho 64-553, 64-554, 64-555 and 64-556 and imidazole couplers described in U.S. Pat. No. 4,818,672 are also usable.

Typical examples of the polymerized color-forming couplers are described in, for example, U.S. Pat. Nos. 3,451, 820, 4,080,211, 4,367,282, 4,409,320 and 4,576,910, British Patent No. 2,102,137 and European Patent No. 341,188A.

The couplers capable of forming a colored dye having a suitable diffusibility are preferably those described in U.S. Pat. No. 4,366,237, British Patent No. 2,125,570, European Patent No. 96,570 and West German Patent (Publication) No. 3,234,533.

Colored couplers used for compensation for unnecessary absorption of the colored dye are preferably those described in Research Disclosure No. 17643, VII-G and No. 307105, VII-G, U.S. Pat. No. 4,163,670, J.P, KOKOKU No. Sho 57-39413, U.S. Pat. Nos. 4,004,929 and 4,138,258 and British Patent No. 1,146,368. Other couplers preferably used herein include couplers capable of compensating for an unnecessary absorption of the colored dye with a fluorescent dye released during the coupling as described in U.S. Pat. No. 4,774,181 and couplers having, as a removable group, a dye precursor group capable of forming a dye by reacting with a developing agent as described in U.S. Pat. No. 4,777,120.

Further, compounds which release a photographically useful residue during a coupling reaction are also preferably usable in the present invention. DIR couplers which release a development inhibitor are preferably those described in the patents shown in the above described RD 17643, VII-F and No. 307105, VII-F as well as those descried in J.P. KOKAI Nos. Sho 57-151944, 57-154234, 60-184248, 63-37346 and 63-37350 and U.S. Pat. Nos. 4,248,962 and 4,782,012.

The couplers which release a bleaching accelerator as described in R.D. Nos. 11449 and 24241 and J.P. KOKAI No. Sho 61-201247 are effective in reducing the time necessitated for a bleaching processing step and they are particularly effective when they are incorporated into a photosensitive material containing the above-described tabular silver halide grains. The couplers which release a nucleating agent or a development accelerator in the image-form in the development step are preferably those described in British Patent Nos. 2,097,140 and 2,131,188 and J.P. KOKAI Nos. Sho 59-157638 and Sho 59-170840. Further, compounds capable of releasing a fogging agent, development accelerator, solvent for silver halides, etc. upon the oxidation-reduction reaction with an oxidate of a developing agent as described in J.P. KOKAI Nos. Sho 60-107029, Sho 60-252340, Hei 1-44940 and Hei 1-45687 are also preferred.

The developing agent of the present invention is useful in particular for preventing soft degradation of yellow images particularly appearing in cases where a compound capable of releasing a development inhibitor or precusors thereof in reaction with an oxidized developing agent is contained in a photosensitive layer which forms yellow images.

Other compounds usable for the photosensitive material according to the present invention include competing couplers described in U.S. Pat. No. 4,130,427, polyequivalent couplers described in U.S. Pat. Nos. 4,283,472, 4,338,393 and 4,310,618, DIR redox compound-releasing couplers, DIR coupler-releasing couplers, DIR coupler-releasing redox compounds and DIR redox-releasing redox compounds described in J.P. KOKAI Nos. Sho 60-185950 and Sho 62-24252, couplers which release a dye that restores the color after coupling-off as described in European Patent Nos. 173,302 A and 313,308 A, ligand-releasing couplers described in U.S. Pat. No. 4,555,477, leuco dye-releasing couplers described in J.P. KOKAI No. Sho 63-75747 and fluorescent dye-releasing couplers described in U.S. Pat. No. 4,774,181.

The couplers used in the present invention can be incorporated into the photosensitive material by various known dispersion methods.

High-boiling solvents used for an oil-in-water dispersion method are described in, for example, U.S. Pat. No. 2,322,027. The high-boiling organic solvents having a boiling point under atmospheric pressure of at least 175° C. and usable in the oil-in-water dispersion method include, for example, phthalates [such as dibutyl phthalate, dicyclohexyl phthalate, di-2-ethylhexyl phthalate, decylphthalate, bis(2,4-di-t-amylphenyl) phthalate, bis(2,4-di-t-amylphenyl) isophthalate and bis(1,1-diethylpropyl)phthalate], phosphates and phosphonates [such as triphenyl phosphate, tricresyl phosphate, 2-ethylhexyldihenyl phosphate, tricyclohexyl phosphate, tri-2-ethylhexyl phosphate, tridodecyl phoshate, tributoxyethyl phosphate, trichloropropyl phosphate and di-2-ethylhexylphenyl phosphate], benzoates [such as 2-ethylhexyl benzoate, dodecyl benzoate and 2-ethylhexyl-p-hydroxybenzoate], amides [such as N,N-di ethyldodecaneamide, N,N-diethyllaurylamide and N-tetradecylpyrrolidone], alcohols and phenols [such as isostearyl alcohol and 2,4-di-tert-amylphenol], aliphatic carboxylates [such as bis(2-ethylhexyl) sebacate, dioctyl azelate, glycerol tributyrate, isostearyl lactate and trioctyl citrate], aniline derivatives [such as N,N-dibutyl-2-butoxy-5-tert-octylaniline] and hydrocarbons [such as paraffin, dodecylbenzene and diisopropylnaphthalene]. Co-solvents usable in the present invention include, for example, organic solvents having a boiling point of at least about 30° C., preferably 50 to about 160° C. Typical examples of them include ethyl acetate, butyl acetate, ethyl propionate, methyl ethyl ketone, cyclohexanone, 2-ethoxyethyl acetate and dimethylformamide.

The steps and effects of the latex dispersion method and examples of the latices usable for the impregnation are described in, for example, U.S. Pat. No. 4,199,363 and West German Patent Application (OLS) Nos. 2,541,274 and 2,541,230.

The color photosensitive material used in the present invention preferably contains phenethyl alcohol or an antiseptic or mold-proofing agent described in J.P. KOKAI Nos. Sho 63-257747, Sho 62-272248 and Hei 1-80941 such as 1,2-benzoisothiazolin-3-one, n-butyl p-hydroxybenzoate, phenol, 4-chloro-3,5-dimethylphenol, 2-phenoxyethanol or 2-(4-thiazolyl) benzimidazole.

The present invention is applicable to various color photosensitive materials such as ordinary color negative films, cinema color negative films, reversal color films for slides or televisions, color papers, positive color films and reversal color papers.

Suitable supports usable in the present invention are described, for example, on page 28 of the above-described RD. No. 17643, from right column, page 647 to left column, page 648 of RD. No. 18716 and on page 879 of RD. No. 307105.

The photosensitive material of the present invention has a total thickness of the hydrophilic colloidal layers on the emulsion layer-side of 28 μm or below, preferably 23 μm or below, more preferably 18 μm or below and particularly 16 μm or below. The film-swelling rate $T_{1/2}$ is preferably 30 sec or below, more preferably 20 sec or below. The thickness is determined at 25° C. and at a relative humidity of 55% (2 days). The film-swelling rate $T_{1/2}$ can be determined by a method known in this technical field. For example, it can be determined with a swellometer described on pages 124 to 129 of A. Green et al., "Photogr. Sci. Eng.", Vol. 19, No. 2. $T_{1/2}$ is defined to be the time required for attaining the thickness of a half (½) of the saturated film thickness (the saturated film thickness being 90% of the maximum thickness of the film swollen with the color developer at 30° C. for 3 minute 15 seconds).

The film-swelling rate $T_{1/2}$ can be controlled by adding a hardener to gelatin used as the binder or by varying the time conditions after the coating. The swelling rate is preferably 150 to 400%. The swelling rate is calculated according to the following formula:

$$[(\text{maximum swollen film thickness}) - (\text{film thickness})]/(\text{film thickness})$$

wherein the maximum swollen film thickness is determined under the above-described conditions.

The photosensitive material used in the present invention preferably has a hydrophilic colloid layer (in other words, back layer) having total thickness of 2 to 20 μm on dry basis on the opposite side to the emulsion layer. The back layer preferably contains the above-described light absorber, filter dye, ultraviolet absorber, antistatic agent, hardener, binder, plasticizer, lubricant, coating aid, surfactant, etc. The swelling rate of the back layer is preferably 150 to 500%.

The photographic processing agents used in the present invention can be those known in the art such as a color developer, black-and-white developer, bleaching solution, fixing solution, bleach-fixing solution, compensating solution and stabilizing solution.

These processing agents may be fed in the form of the liquid or, alternatively, in the form of a powder or granules. When they are used in the liquid form, they may be either a concentrated solution or the solution to b e directly used.

The color developing solution generally contains, in addition to the color developing agent, a pH buffering agent such as alkali metal carbonates, borates and phosphates, a development inhibitor such as bromide salts, iodide salts, benzimidazoles, benzthiazoles and mercapt compounds, and an antifoggant, and the like. Further, if desired, the developing solution may contain a preservative such as substituted hydroxylamines (for example, hydroxylamine, diethyl hydroxylamine, disodium N,N-bis (sulfonate ethyl) hydroxylamine), hydrazine sulfites, phenylsemicarbazides, triethanolamine, catechol sulfonic acids, triethylenediamine (1,4-azabicyclo[2,2,2]octane); an organic solvent such as ethyleneglycol and diethyleneglycol; a development accelerator such as quaternary ammonium salts and amines; a dye forming coupler; a competing coupler; a foggant such as sodium boron hydride; an assistant developing agent such as 1-phenyl-3-pyrazolidone; thickening agent; various chelating agents represented by aminopolycarboxylic acids, aminopolyphosphonic acids, alkylphosphonic acids and phosphonocarboxylic acids, for example, ethylenediaminetetraacetic acid, nitrilotriacetic acid, diethylenetriamine pentaacetic acid, cyclohexanediamine tetraacetic acid, hydroxyethylimino diacetic acid, carboxyethylimino diacetic acid, 1-hydroxyethylydene-1,1-diphosphonic acid, nitrilo-N,N,N'-trimethylenephosphonic acid, ethylenediamine-N,N,N',N'-tetramethylene phosphonic acid, ethylenediamine-dig(-hydroxyphenylacetic acid) and salts thereof.

Rapid processing of high level can be achieved by use of the color developing agent of the present invention, in particular, in cases where bromine ions which are development inhibitors present in a color developing solution in a concentration of 10 mmol to 60 mmol/liter (In these cases, the bromine ions are released into the color developing solution from the photographic materials by developing silver halides in the photographic materials).

The black-and-white developer used for the reversal process may contain known black-and-white developing agents such as dihydroxybenzenes, e.g. hydroquinone, 3-pyrazolidones, e.g. 1-phenyl-3-pyrazolidone, and aminophenols, e.g. N-methyl-p-aminophenol. They can be used either singly or in combination of them.

The pH of the color developer and black-and-white developer is usually in the range of 9 to 12. The amount of the replenisher for the developer which varies depending on the color photosensitive material to be processed is usually 1 l or below per square meter of the photosensitive material. It can be reduced to 500 ml or further to 100 ml or below by reducing bromide ion concentration in the replenisher.

In the color image-forming method of the present invention, the color development process is not particularly limited and any known method can be employed. It is preferred, however, to continuously conduct the development while the developer is replenished.

The color development is usually followed by bleaching. The bleaching process can be conducted simultaneously with the fixing process (bleach-fixing process) or separately from it. For the acceleration, the bleach-fixing process may be conducted after the bleaching process. Depending on the purpose, two bleach-fixing vessels connected with each other can be employed; the fixing process can be conducted prior to the bleach-fixing process; or the bleaching process can be conducted after the bleach-fixing process. Examples of the bleaching agents include compounds of polyvalent metals such as iron (III), and peracids. Typical examples of the bleaching agents include organic complex salts of iron (III) such as aminopolycarboxylates, e.g. ethylenediaminetetraacetate, diethylenetriaminepentaacetate, cyclohexanediaminetetraacetate, methyliminodiacetate, 1,3-diaminopropanetetraacetate, glycol ether diaminetetraacetate and carboxylethyliminodiacetate; persulfates and hydrogen peroxide. The iron (III) complex salts of aminopolycarboxylic acids are particularly effective in both bleaching solution and bleach-fixing solution. The pH of the bleaching solution or bleach-fixing solution containing such an iron (III) complex salt of aminopolycarboxylic acid is usually 5.5 to 8. For accelerating the process or for processing the photosensitive material having a high silver chloride content, a pH in the range of 4.5 to 6.5 can also be employed.

In particular, where total carbon atoms of $R_1$, $R_2$ and $R_3$ in the formula (D1) is the same as that of $R_4$, $R_5$ and $R_6$ in the formula (D2), an amount of the color developing agent remaining in the developed photographic materials lowers by use of the developing agent of the formula (D2), compared with the cases using the developing agent of the formula (D1). In this connection, the differences appear more greatly in cases of using a breaching solution or breaching and fixing solution having a low pH, for example, pH of 4.5 to 6.5. Since the amount of the color developing agent remaining in the developed photographic materials adversely affects the storability with elapse of time (production of stain, decoloring of formed image, spreading and fading of image with elapse of time), it is preferable that the remaining amount should be as low as possible. In this respect, it is surprising that an amount of the color developing agent remaining in the developed photographic materials can be lowered by use of the developing agent of the present invention such as formula (D2) wherein a plurality of hydroxyl groups are introduced into one of alkyl groups in the developing agent.

If desired, a bleaching accelerators may be incorporated into a bleaching solution, bleaching and fixing solution or their preceeding bath. Examples of useful bleaching accelerators are described in the following specifications: compounds having a mercapt group or disulfide bond described in U.S. Pat. No. 3,893,858, German Patent No. 1,290,812, JP Kokai No. 53-95630 and Research Disclosure No. 17,129 (1978, July); thiazolidine derivatives in JP Kokai No. 50-140129; thiourea derivatives in U.S. Pat. No. 3,706,561; iodide salts in JP Kokai No. 58-16235; polyoxyethylene compounds in German Patent 2,748,430; polyamine compounds in JP Kokoku No. 45-8836; and bromide ions and the like. Among the bleaching accelerators, those having a mercapto group or disulfido group are preferred, since they have a remarkable acceleration effect. Compounds described in U.S. Pat. No. 3,893,858, West German Patent No. 1,290, 812 and J.P.KOKAI No. Sho 53-95,630 are particularly preferred. Further, compounds described in U.S. Pat. No. 4,552,834 are also preferred. These bleaching accelerators are particularly effective when a color photosensitive material for photography is to be bleached or bleach-fixed.

The fixing agents include, for example, thiosulfates, thiocyanates, thioether compounds, thioureas and a large amount of iodides. Among them, the thiosulfates are commonly used and ammonium thiosulfate is most widely usable. Preferred examples of the preservatives for the bleach-fixing solution include sulfites, hydrogensulfites, sulfinic acids and carbonylhydrogensulfite adducts.

The photosensitive silver halide material for color photography of the present invention is usually subjected to washing with water and/or stabilization step after the desilverization.

Although the amount of water necessitated for washing can be remarkably reduced by the multi-stage counter flow system described in the above-described journal, another problem is caused in this method that bacteria propagate themselves while water is kept for a longer time in the tanks and, as a result, a suspended matter thus formed is fixed on the photosensitive material. For solving this problem, a very effective method for reducing the amount of calcium ion and magnesium ion described in J.P. KOKAI No. Sho 62-288838 can be employed. Further, this problem can be solved also by using isothiazolone compounds described in J.P. KOKAI No. Sho 57-8542, thiabendazoles, chlorine-containing germicides such as chlorinated sodium isocyanurates, benzotriazoles and germicides described in Hiroshi Horiguchi "Bokin Bobai-zai no Kagaku", "Biseibutsu no Mekkin, Sakkin, Bobai Gijutsu" edited by Eisei Gijutsu-kai and "Bokinbobai-sai Jiten" edited by Nippon Bokinbobai Gakkai.

The pH of washing water used for processing the photosensitive material is 4 to 9, preferably 5 to 8. The temperature of water to be used for washing and the washing time which vary depending on the properties and use of the photosensitive material are preferably in the ranges of 30 to 45° C. and 30 sec to 5 min, respectively. The photosensitive material can be processed directly with a stabilizing solution in place of washing with water. The stabilization can be conducted by any of known processes described in J.P. KOKAI Nos. Sho 57-8543, 58-14834 and 60-220345.

The washing process with water may be followed by a stabilization process. In the stabilization, a stabilizing bath containing formalin or a compound usable as a substitute for formalin and a surfactant which is usually used as the final bath for a photosensitive material for color photography can be used. Also the stabilizing bath may contain a chelating agent and a mold-proofing agent.

The temperature of the processing solutions used in the present invention are controlled at 10 to 50° C. The standard temperature is usually 33 to 38° C., but a higher temperature can be employed to accelerate the process and thereby to reduce the process time or, on the contrary, a lower temperature can also be employed to improve the quality of the image and stability of the processing liquid.

Typical examples of the processing solutions such as bleach-fixing solutions used in the present invention are given in Akira Sasai, "Shashin Kogyo Bessatsu, Saishin Shashin Shoho Binran" (published by Shashin Kogyo Shuppan-sha on Jul. 20, 1983).

Examples of typical processing agents usable in the present invention will be described below.

As the bleaching solutions, fixing solutions and stabilizers for color negative films, those described in J.P. KOKAI No. Hei 4-359249, particularly, bleaching replenisher, fixing replenisher and stabilizer No. 18 described in Example 1 are usable. They may be fed into the vessel as they are or after concentration. For example, the above-described stabilizer No.18 may be concentrated to 100-fold concentration.

As the bleach fixing solutions for color papers, those described in J.P. KOKAI No. Hei 4-195037, particularly bleach fixing replenishers described in the Examples, particularly Example 2, are usable.

As the bleach-fixing solution and water for washing for the direct positive color photosensitive materials, bleach-fixing solutions described in J.P. KOKAI No. 3-13941 (bleach-fixing solutions in Examples, particularly Example 1), and water for washing described in J.P. KOKAI No. 3-13941, particularly Example 1, are usable,, respectively. These processing solutions may be fed into the vessel as they are or after concentration.

The above-described processing solutions are usable for the development of various photosensitive materials such as photographic color photosensitive materials, e.g. color negative films and color reversal films, and printing color photosensitive materials, e.g. color papers, color reversal papers and direct positive color photosensitive materials. The following Examples will further illustrate the present invention, which by no means limit the invention.

EXAMPLE 1

A primed cellulose triacetate film support was coated with compositions given below to form a laminate, thereby obtaining a multilayer color photosensitive material, which will be referred to as "sample 101":

(Compositions of Photosensitive Layers)

Main materials to be used for forming the layers are classified as follows:

ExC: cyan coupler
ExM: magenta coupler
ExY: yellow coupler
ExS: sensitizing dye

UV: ultraviolet absorber
HBS: high-boiling organic solvent
H: gelatin hardener

The numerals for the respective components indicate the amount of coating given by g/m². Those for silver halides are given in terms of silver. Those for sensitizing dyes are given in terms of molar unit per mol of the silver halide contained in the same layer.

(Sample 101)
The First Layer (Antihalation Layer):

|  |  |  |  |
|---|---|---|---|
| black colloidal silver | silver 0.18 | | |
| glatin | 1.40 | | |
| ExM-1 | 0.11 | | |
| ExF-1 | 3.4 | ×10⁻³ | |
| HBS-1 | 0.16 | | |

The Second Layer (Intermediate Layer):

|  |  |
|---|---|
| ExC-2 | 0.030 |
| UV-1 | 0.020 |
| UV-2 | 0.020 |
| UV-3 | 0.060 |
| HBS-1 | 0.05 |
| HBS-2 | 0.0200 |
| polyethyl acrylate latex | 0.080 |
| gelatin | 0.90 |

The Third Layer (Low-Speed Red-Sensitive Emulsion Layer)

|  |  |  |
|---|---|---|
| emulsion A | silver 0.23 | |
| emulsion B | silver 0.23 | |
| ExS-1 | 5.0 | ×10⁻⁴ |
| ExS-2 | 1.8 | ×10⁻⁵ |
| ExS-3 | 5.0 | ×10⁻⁴ |
| ExC-1 | 0.050 | |
| ExC-3 | 0.030 | |
| ExC-4 | 0.14 | |
| ExC-5 | 3.0 | ×10⁻³ |
| ExC-7 | 1.0 | ×10⁻³ |
| ExC-8 | 0.010 | |
| Cpd-2 | 0.005 | |
| HBS-1 | 0.08 | |
| gelatin | 0.80 | |

The Fourth Layer (Medium-Speed Red-Sensitive Emulsion Layer)

|  |  |  |
|---|---|---|
| emulsion C | silver 0.70 | |
| ExS-1 | 3.4 | ×10⁻⁴ |
| ExS-2 | 1.2 | ×10⁻⁵ |
| ExS-3 | 4.0 | ×10⁻⁴ |
| ExC-1 | 0.15 | |
| ExC-2 | 0.060 | |
| ExC-4 | 0.050 | |
| ExC-5 | 0.010 | |
| ExC-8 | 0.010 | |
| Cpd-2 | 0.023 | |
| HBS-1 | 0.08 | |
| gelatin | 0.55 | |

The Fifth Layer (High-Speed Red-Sensitive Emulsion Layer)

|  |  |  |
|---|---|---|
| emulsion D | silver 1.62 | |
| ExS-1 | 2.4 | ×10⁻⁴ |
| ExS-2 | 1.0 | ×10⁻⁵ |
| ExS-3 | 3.0 | ×10⁻⁴ |
| ExC-1 | 0.10 | |
| ExC-3 | 0.050 | |
| ExC-5 | 2.0 | ×10⁻³ |
| ExC-6 | 0.010 | |
| ExC-8 | 0.010 | |
| Cpd-2 | 0.025 | |
| HBS-1 | 0.20 | |
| HBS-2 | 0.10 | |
| gelatin | 1.30 | |

The Sixth Layer (Intermediate Layer)

|  |  |
|---|---|
| Cpd-1 | 0.090 |
| HBS-1 | 0.05 |
| polyethyl acrylate latex | 0.15 |
| gelatin | 1.10 |

The Seventh Layer (Low-Speed Green-Sensitive Emulsion Layer)

|  |  |  |
|---|---|---|
| emulsion E | silver 0.24 | |
| emulsion F | silver 0.24 | |
| ExS-4 | 4.0 | ×10⁻⁵ |
| ExS-5 | 1.8 | ×10⁻⁴ |
| ExS-6 | 6.5 | ×10⁻³ |
| ExM-1 | 5.0 | ×10⁻³ |
| ExM-2 | 0.28 | |
| ExM-3 | 0.086 | |
| ExM-4 | 0.030 | |
| ExY-1 | 0.015 | |
| HBS-1 | 0.30 | |
| HBS-3 | 0.010 | |
| gelatin | 0.85 | |

The Eighth Layer (Medium-Speed Green-Sensitive Emulsion Layer)

|  |  |  |
|---|---|---|
| emulsion G | silver 0.94 | |
| EXS-4 | 2.0 | ×10⁻⁵ |
| ExS-5 | 1.4 | ×10⁻⁴ |
| ExS-6 | 5.4 | ×10⁻⁴ |
| ExM-2 | 0.14 | |
| ExM-3 | 0.045 | |
| ExM-5 | 0.020 | |
| ExY-1 | 7.0 | ×10⁻³ |
| ExY-4 | 2.0 | ×10⁻³ |
| ExY-5 | 0.020 | |
| HBS-1 | 0.16 | |
| HBS-3 | 8.0 | ×10⁻³ |
| gelatin | 0.80 | |

The Ninth Layer (High-Speed Green-Sensitive Emulsion Layer)

|  |  |  |
|---|---|---|
| emulsion H | silver 1.29 | |
| ExS-4 | 3.7 | ×10⁻⁵ |
| ExS-5 | 8.1 | ×10⁻⁵ |
| ExS-6 | 3.2 | ×10⁻⁴ |
| ExC-1 | 0.010 | |
| ExM-1 | 0.020 | |

-continued

| | |
|---|---|
| ExM-4 | 0.050 |
| ExM-5 | 0.020 |
| ExY-4 | 5.0 ×10⁻³ |
| Cpd-3 | 0.050 |
| HBS-1 | 0.20 |
| HBS-2 | 0.08 |
| polyethyl acrylate latex | 0.26 |
| gelatin | 1.45 |

The Tenth Layer (Yellow Filter Layer)

| | | |
|---|---|---|
| yellow colloidal silfer | silver 7.5 | ×10⁻³ |
| Cpd-1 | 0.13 | |
| Cpd-4 | 7.5 | ×10⁻³ |
| HBS-1 | 0.60 | |
| gelatin | 0.60 | |

The Eleventh Layer (Low-Speed Blue-Sensitive Emulsion Layer)

| | | |
|---|---|---|
| emulsion I | silver 0.25 | |
| emulsion J | silver 0.25 | |
| emulsion K | silver 0.10 | |
| ExS-7 | 8.0 | ×10⁻⁴ |
| ExC-7 | 0.010 | |
| ExY-1 | 5.0 | ×10⁻³ |
| ExY-2 | 0.40 | |
| ExY-3 | 0.45 | |
| ExY-4 | 6.0 | ×10⁻³ |
| ExY-6 | 0.10 | |
| HBS-1 | 0.30 | |
| gelatin | 1.65 | |

The Twelfth Layer (High-Speed Blue-Sensitive Emulsion Layer)

| | | |
|---|---|---|
| emulsion L | silver 1.30 | |
| ExS-7 | 3.0 | ×10⁻⁴ |
| ExY-2 | 0.15 | |
| ExY-3 | 0.06 | |
| ExY-4 | 5.0 | ×10⁻³ |
| Cpd-2 | 0.10 | |
| HBS-1 | 0.070 | |
| gelatin | 1.20 | |

The Thirteenth Layer (The First Protective Layer)

| | |
|---|---|
| UV-2 | 0.10 |
| UV-3 | 0.12 |
| UV-4 | 0.30 |
| HBS-1 | 0.10 |
| gelatin | 2.50 |

The Fourteenth Layer (the Second Protective Layer)

| | |
|---|---|
| emulsion M | silver 0.10 |
| H-1 | 0.37 |
| B-1 (diameter: 1.7 μm) | 5.0 ×10⁻² |
| B-2 (diameter: 1.7 μm) | 0.15 |
| B-3 | 0.05 |

-continued

| | |
|---|---|
| g-1 | 0.20 |
| gelatin | 0.70 |

Further, the respective layers suitably contain W-1 to W-3, B-4 to B-6, F-1 to F-17, iron salts, lead salts, gold salts, platinum salts, iridium salts, palladium salts and rhodium salts in order to improve the storability, processability, pressure resistance, mildew-proofing and bacteria-proofing properties, antistatic properties and coating easiness.

Cpd-4 was dispersed in solid form according to a method of International Patent No. 88-4794.

TABLE 1

| E-mulsion | Shape of grains (halogen structure) | Average AgI content (%) | Coefficient variation of iodine distribution among grains (%) |
|---|---|---|---|
| A | Round tabular (homogeneous structure) | 0 | — |
| B | Cubic (double structure having shell of high iodine content) | 1.0 | — |
| C | Tetradecahedral (triple structure having intermediate shell of high iodine content) | 4.5 | 25 |
| D | Hexagonal tabular (outside having high iodine content) | 2.0 | 16 |
| E | Round tabular (outside having high iodine content) | 1.0 | — |
| F | Octahedral (double structure having core of high iodine content) | 6.0 | 22 |
| G | Tetradecahedral (triple structure having intermediate shell of high iodine content) | 4.5 | 19 |
| H | Hexagonal tabular (outside having high iodine content) | 3.5 | 16 |
| I | Round tabular (central part having high iodine content) | 2.0 | 15 |
| J | Cubic (homogeneous structure) | 1.0 | 10 |
| K | Tetradecahedral (double structure having core of high iodine content) | 18.0 | 8 |
| L | Hexagonal tabular (triple structure having core of high iodine content) | 12.0 | 12 |
| M | Insensitive fine grain (homogeneous structure) | 1.0 | — |

| E-mulsion | Shape of grains (halogen structure) | Average grain diameter (μm) | Coefficient of variation of grain diameter (%) | Diameter/thickness ratio |
|---|---|---|---|---|
| A | Round tabular (homogeneous structure) | 0.45 | 15 | 5.5 |
| B | Cubic (double structure having shell of high iodine content) | 0.20 | 8 | 1 |
| C | Tetradecahedral (triple structure having intermediate shell of high iodine content) | 0.85 | 18 | 1 |
| D | Hexagonal tabular (outside having high iodine content) | 1.10 | 17 | 7.5 |
| E | Round tabular (outside having high iodine content) | 0.45 | 15 | 3.0 |
| F | Octahedral (double structure having core of high iodine content) | 0.25 | 8 | 1 |
| G | Tetradecahedral (triple structure having intermediate shell of high iodine content) | 0.85 | 19 | 1 |
| H | Hexagonal tabular (outside having high iodine content) | 1.10 | 16 | 6.8 |
| I | Round tabular (central part having high iodine content) | 0.45 | 15 | 6.0 |
| J | Cubic (homogeneous structure) | 0.30 | 8 | 1 |
| K | Tetradecahedral (double structure | 0.80 | 18 | 1 |

TABLE 1-continued

| | | | | |
|---|---|---|---|---|
| | having core of high iodine content) | | | |
| L | Hexagonal tabular (triple structure having core of high iodine content) | 1.35 | 22 | 12.0 |
| M | Insensitive fine grain (homogeneous structure) | 0.04 | 15 | 1 |

In Table 1:

(1) The emulsions I to L were reduction-sensitized with thiourea dioxide and thiosulfonic acid in the step of preparation of the grains by a method described in an Example of J.P. KOKAI No. Hei 2-191938.

(2) The emulsions A to L were sensitized by gold sensitization, sulfur sensitization and selenium sensitization methods in the presence of a spectral sensitizing dye mentioned above for each photosensitive layer and sodium thiocyanate by a method described in an Example of J.P. KOKAI No. Hei 3-237450.

(3) In the preparation of tabular grains, a low-molecular weight gelatin was used as described in an Example of J.P. KOKAI No. Hei 1-158426.

(4) The transition lines as described in J.P. KOKAI No. Hei 3-237450 are obserbed on the tabular grains with a high-voltage electron microscope.

The couplers and additives used in each layer were dispersed in a gelatin solution by a method given in Table 2. The addition method for each layer is given in Table 3.

The structures of the compounds used are as follows:

TABLE 2

Dispersion method

A  A homogeneous aqueous solution containing a coupler, high-boiling organic solvent, surfactant, NaOH, n-propanol and other additives is neutralized to pecipitate and disperse them.

B  A homogeneous solution of a coupler, high-boiling organic solvent and other additives in n-propanol is added to an aqueous surfactant solution to pecipitate and disperse them.

C  A solution containing a coupler, high-boiling organic solvent, surfactant, low-boiling organic solvent and other additives is mixed with an aqueous solution containing gelatin and a surfactant under stirring to conduct emulsification dispersion, and then the low-boiling organic solvent is removed by distillation.

D  This method is the same as the method C except that the organic solvent is removed by washing with water or ultrafiltration after the dispersion.

TABLE 3

| Layer | Dispersion method | Average diameter of dispersed grains (nm) |
|---|---|---|
| The third layer | C | 133 |
| The fourth layer | C | 130 |
| The fifth layer | D | 40 |
| The seventh layer | C | 135 |
| The eighth layer | C | 60 |
| The ninth layer | A | 40 |
| The eleventh layer | C | 125 |
| The twelfth layer | B | 80 |

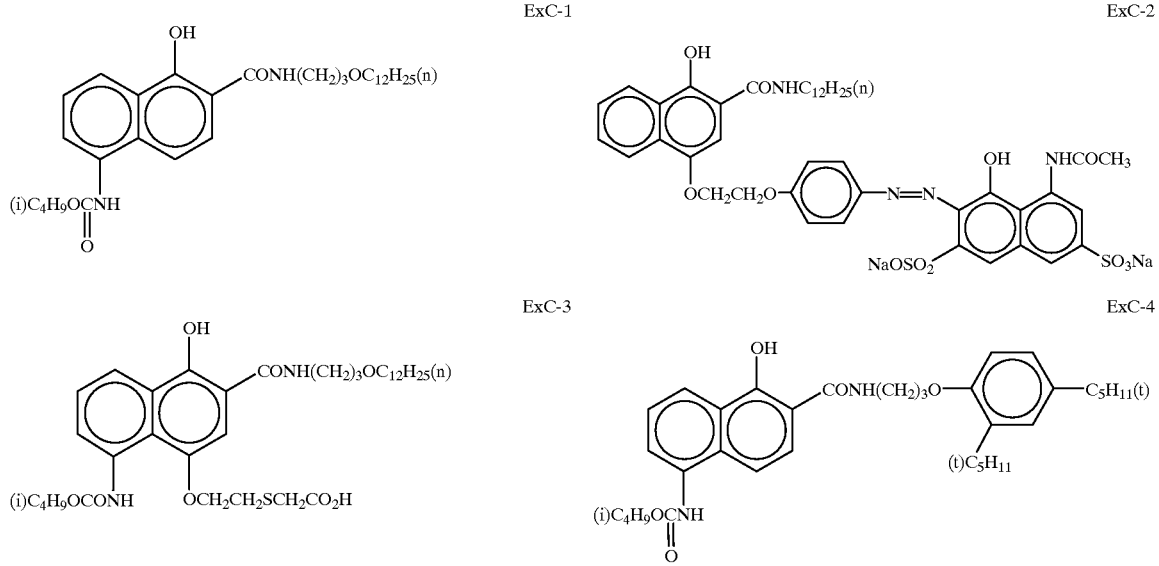

ExC-5
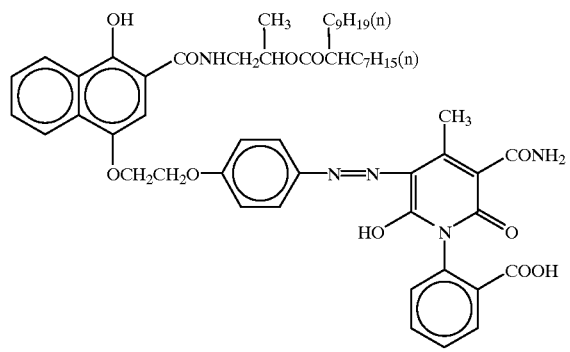
ExC-6
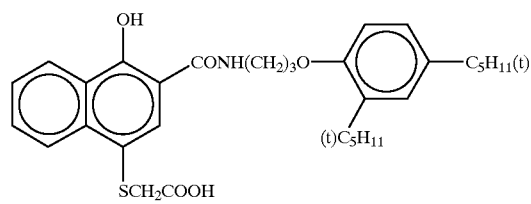
ExC-7
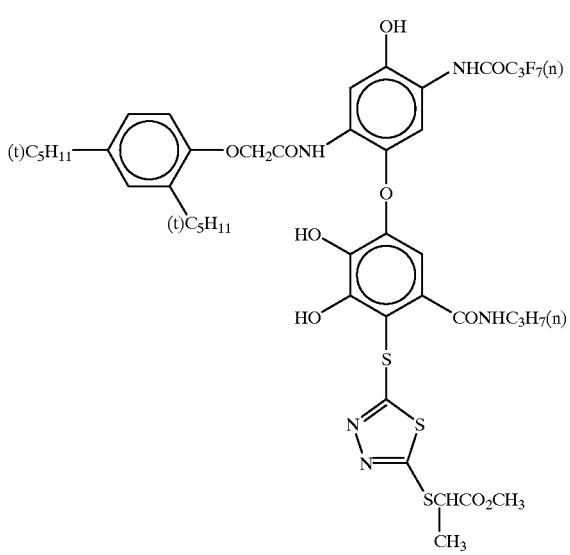
ExC-8
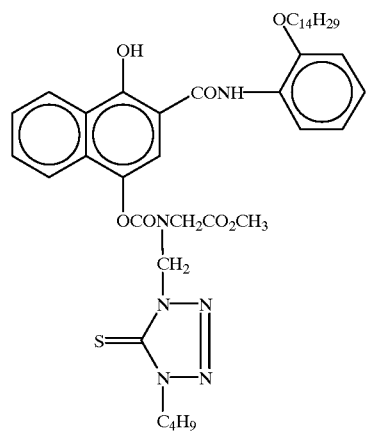
ExM-1
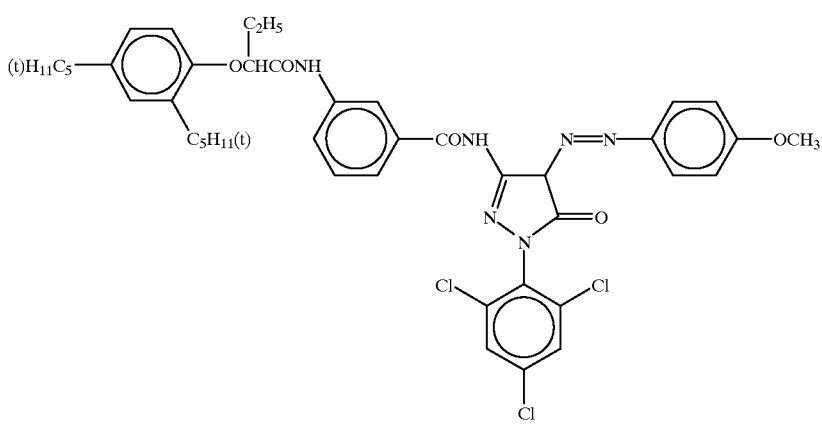

-continued
ExM-2
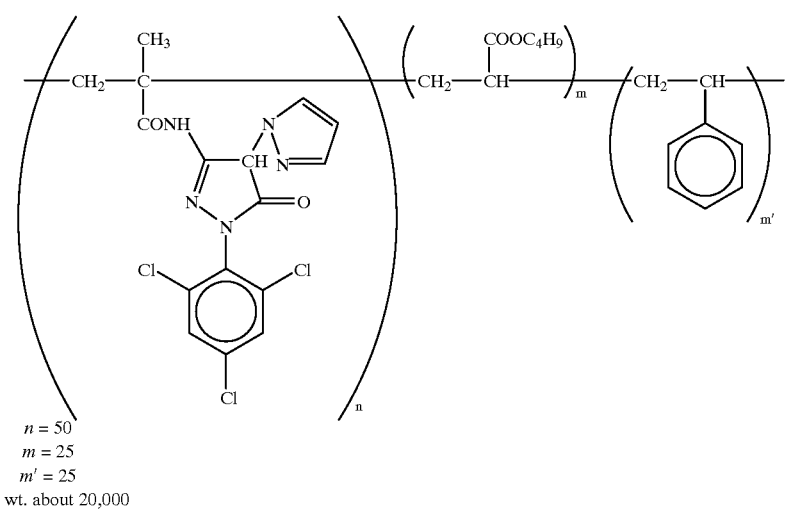
n = 50
m = 25
m' = 25
mol. wt. about 20,000
ExM-3
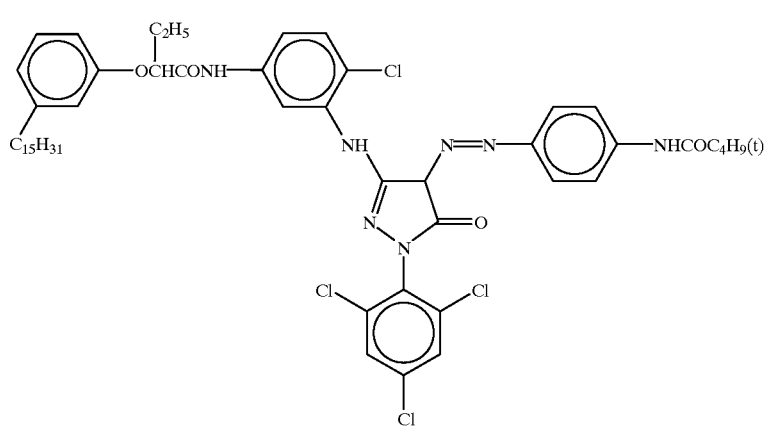
ExM-4
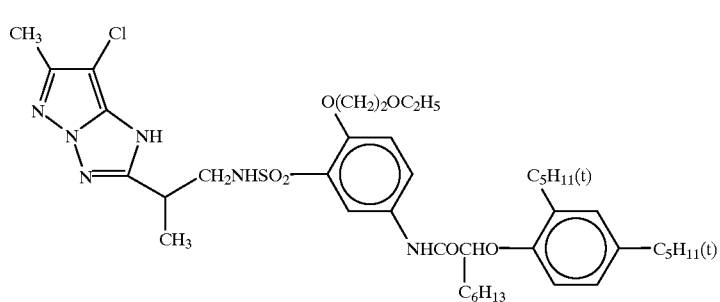
ExM-5
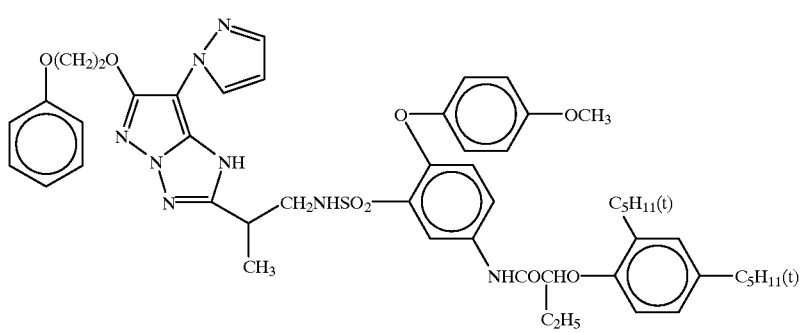

-continued
ExY-1
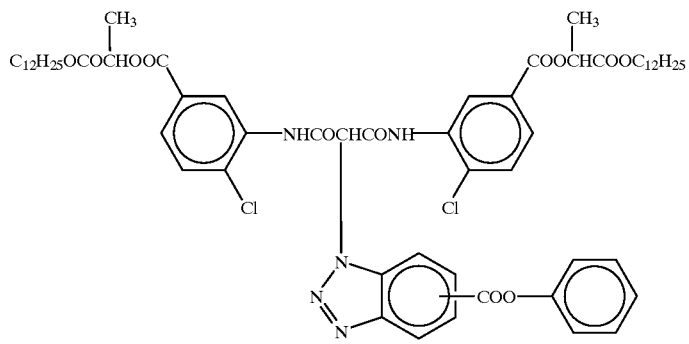
ExY-2
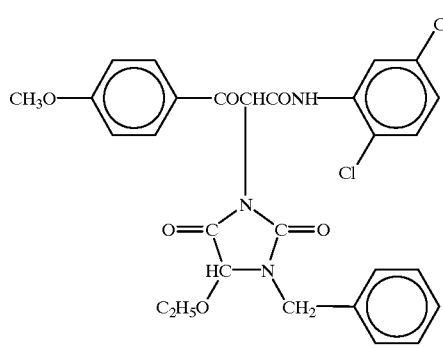
ExY-3
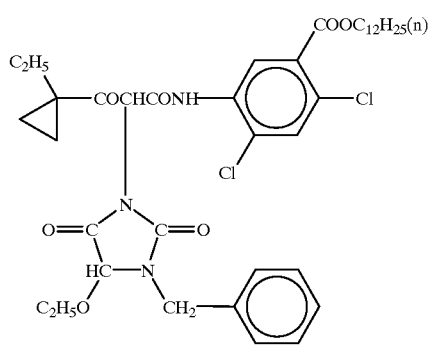
ExY-4
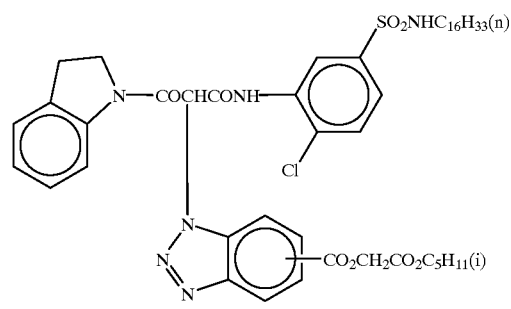
ExY-5
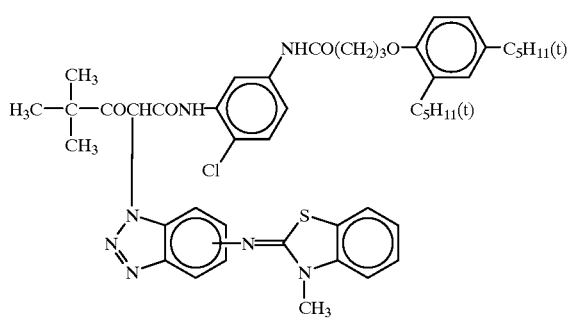
ExY-6
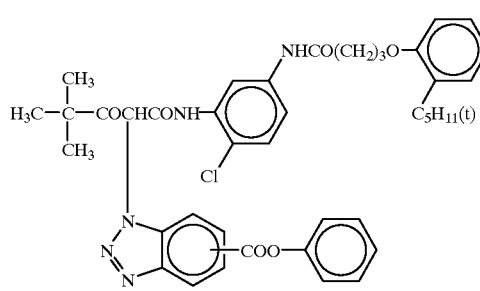
ExF-1
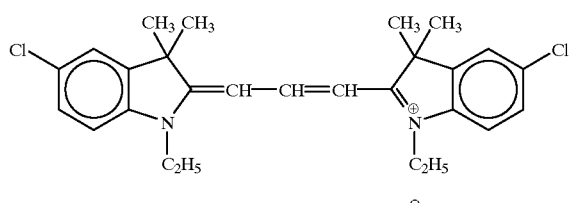

-continued
Cpd-1
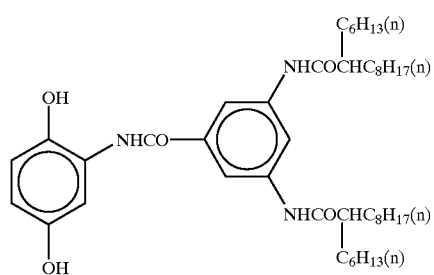
Cpd-2
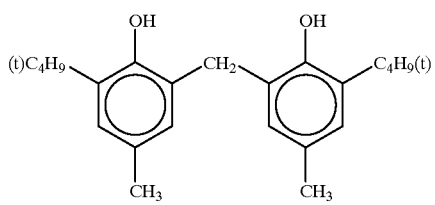
Cpd-3
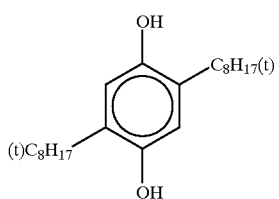
Cpd-4
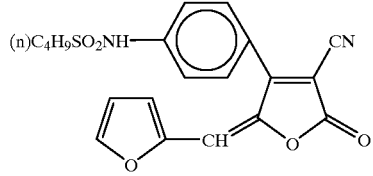
UV-1
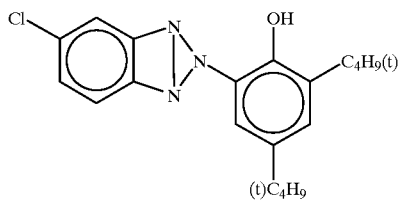
UV-2
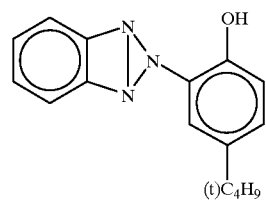
UV-3
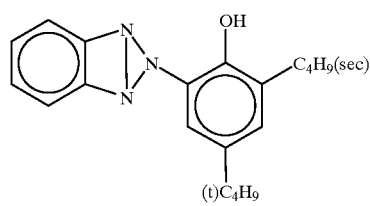
UV-4
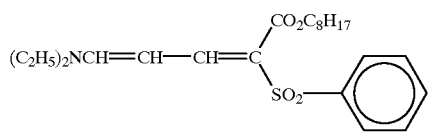
HBS-1
Tricresyl Phosphate
HBS-2
D-n-butyl Phthalate
HBS-3
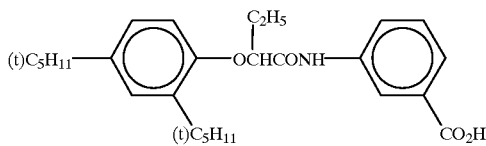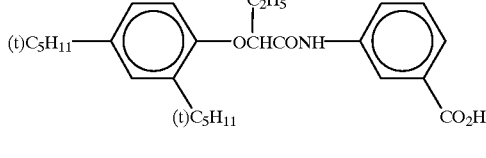
ExS-1
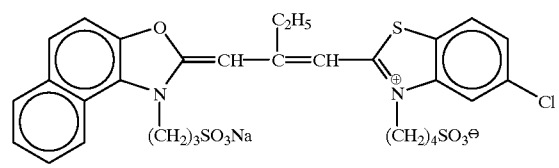
ExS-2
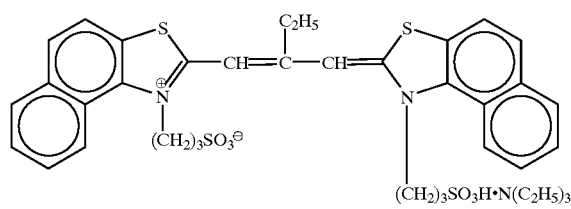
ExS-3

-continued
ExS-4
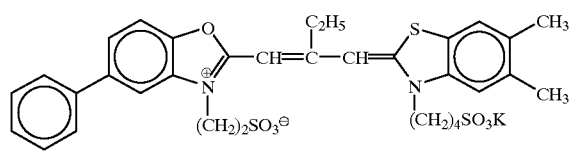
ExS-5
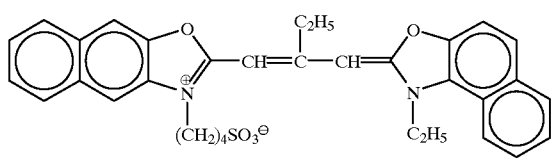
ExS-6
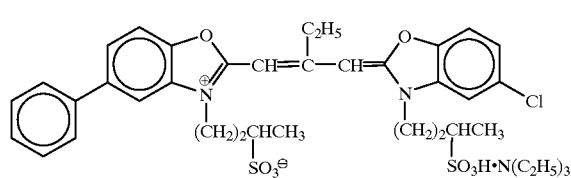
ExS-7
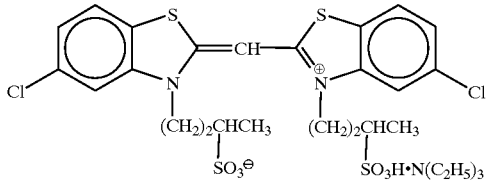
S-1
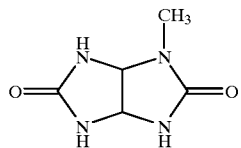
H-1
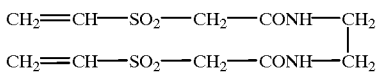
B-1
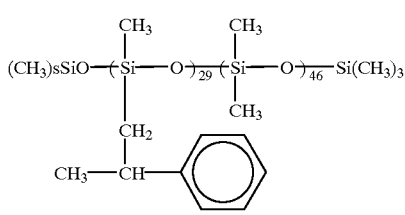
x/y = 10/90
B-2
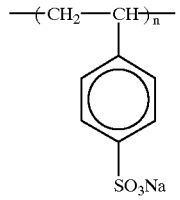
x/y = 40/60
B-3
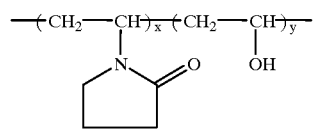
B-4
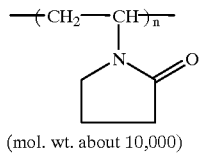
B-5
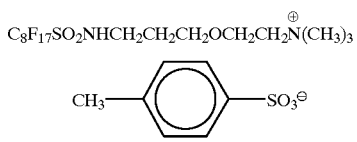
x/y = 70/30
B-6
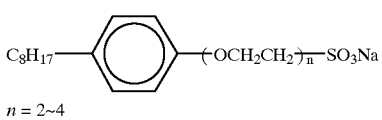
(mol. wt. about 10,000)
W-1
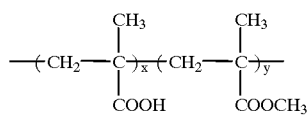
W-2
$C_8H_{17}$—⟨phenyl⟩—$(OCH_2CH_2)_n$—$SO_3Na$
n = 2~4
W-3
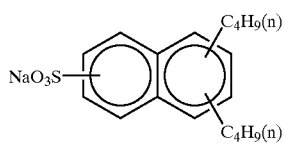
F-1
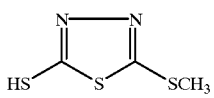

-continued
F-2
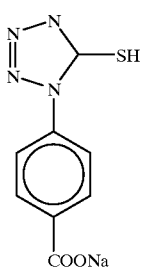
F-3
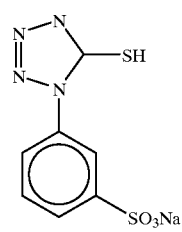
F-4
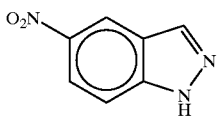
F-5
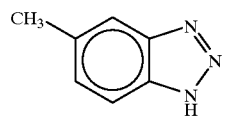
F-6
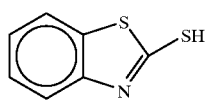
F-7
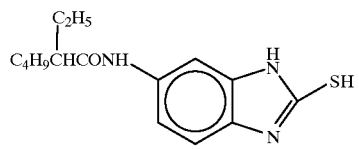
F-8
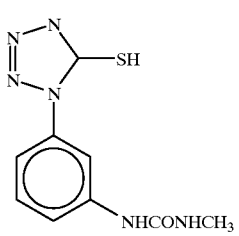
F-9
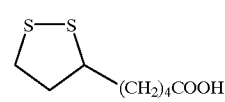
F-10
F-11
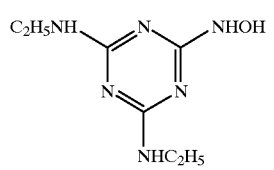
F-12
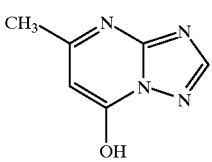
F-13
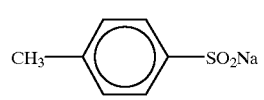
F-14
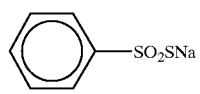
F-15
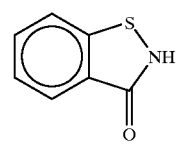
F-16
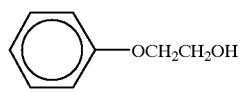
F-17
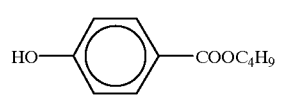

Processing Step:

| (Step) | (Process time) | (Process temp.) | (Amount of replenisher) | (Capacity of tank, l) |
|---|---|---|---|---|
| Color development | 130 sec | 45.0° C. | 140 ml/m² | 2.0 |
| Bleach-fixing | 60 sec | 45.0° C. | 120 ml/m² | 2.0 |
| washing with water (1) | 15 sec | 45.0° C. | — | 0.5 |
| washing with water (2) | 15 sec | 45.0° C. | — | 0.5 |
| washing with water (3) | 15 sec | 45.0° C. | 120 ml/m² | 0.5 |
| Stabilization | 2 sec | Room temp. | coating | |
| Drying | 20 sec | 85° C. | | |

The crossover time from the color development to the bleach-fixing and from bleach-fixing to washing with water (1) was 5 sec.

The average quantity of the processing solution taken out per m² of the photosensitive material was 40 ml.

The washing with water (1) to (3) was conducted by counter-current multi-stage cascade method.

The washing with water (1) to (3) was conducted by a washing tank having a plurality of compartments vertically positioned therein wherein the photosensitive material could be transported in the liquid with a wiper blade without crossing over in air.

As described in J.P. Kokai No. Hei. 3-280042, the compensation for the evaporation was conducted by detecting the temperature and humidity of air outside the processing machine with a thermo-hygrometer and calculating the amount of the evaporated water. Water used for the compensation was ion-exchanged water which was the same as that used in the above-described washing steps.

The composition of each of the processing liquids used for the respective steps was as follows:

| | Mother liquor | Replenisher |
|---|---|---|
| (Color developer) | | |
| Diethylenetriaminepentaacetic acid | 4.0 g | 4.0 g |
| 1-hydroxyethylidene-1,1-diphosphonic acid | 3.0 g | 3.0 g |
| Potassium hydroxide | 10.0 g | 15.0 g |
| Potassium iodide | 1.3 mg | 0 g |
| Potassium bromide | 4.0 g | 0 g |
| Potassium carbonate | 50.0 g | 50.0 g |
| Sodium sulfite | 4.0 g | 6.8 g |
| Hydroxylamine sulfate | 50.0 mmol | 80.0 mmol |
| 4-(N-ethyl-N-β-hydroxyethylamino)-2-methyl-aniline (p-5) sulfate | 40.0 mmol | 55.0 mmol |
| Water | ad 1000 ml | 1000 ml |
| pH | 10.10 | 11.80 |
| (Bleach-fixing bath) | | |
| Bleaching agent (ferric ammonium salt of compound A) | 0.15 mol | 0.20 mol |
| Ferric ammonium ethylenediaminetetraacetate dihydrate | 0.05 mol | 0.07 mol |
| Sulfinic acid (compound B) | 0.1 mol | 0.15 mol |
| Fixing accelerator (compound C) | 0.3 mol | 0.4 mol |
| Ammonium thiosulfate (75%) | 300 ml | 400 ml |
| Ammonium sulfite (75%) | 30 g | 45 g |
| Succinic acid | 30 g | 40 g |

-continued

| | Mother liquor | Replenisher |
|---|---|---|
| Water | ad 1000 ml | 1000 ml |
| pH | 5.00 | 4.60 |

(Washing Water)

Tap water was passed through a mixed bed column packed with an H-type strongly acidic cation exchange resin (Amberlite IR-120B; a product of Rohm & Haas Co.) and an OH-type strongly basic anion exchange resin (Amberlite IR-400; a product of Rohm & Haas Co.) to reduce calcium and magnesium ion concentration to 3 mg/l or below, and then 20 mg/l of sodium isocyanurate dichloride and 150 mg/l of sodium sulfate were added to the water. The pH of the water was in the range of 6.5 to 7.5.

| (Stabilizer) (common to the mother liquid and tank liquid) | |
|---|---|
| Sodium p-toluenesulfinate | 0.03 g |
| Polyoxyethylene-p-monononylphenyl ether (average degree of polymerization: 10) | 0.2 g |
| Disodium ethylenediaminetetraacetate | 0.05 g |
| Water | ad 1000 ml |
| pH | 8.0 |

Silver was recovered from the bleach-fixing bath in line with a silver-recovering apparatus. This apparatus was a small electrolytic silver-recovering apparatus comprising a carbon anode and a stainless steel drum cathode. The current density was 0.5 A/dm².

The structures of the compounds used in the processing steps are as follows:

Compound A

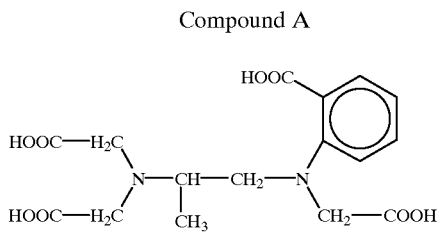

Compound B

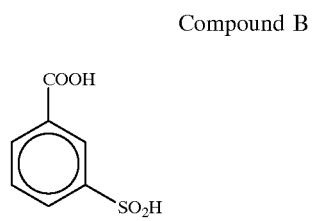

Compound C

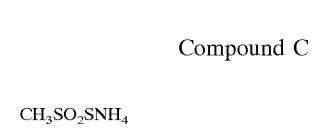

$CH_3SO_2SNH_4$

After an image-forming exposure of the sample 101, the continuous process was conducted until the amount of the bleach-fixing replenisher had become 3-folds of the tank capacity.

The process in which the running solution thus obtained will be referred to as "process 151". Then the same color developer as that described above was prepared except that the color developing agent P-5 contained therein was replaced with the equimolar amount of a comparative color developing agent or the color developing agent of the present invention given in Table 101, and the continuous process was conducted in the same manner as that described above to obtain running solutions (processes 152 to 188).

The rapidity of the process was evaluated as follows: after wedge-exposure of the sample 101, it was processed with each of the running solutions (processes 152 to 188) while the color development time was changed stepwise from 1 minute to 2 minute 10 seconds at intervals of 10 seconds. The optical density of the cyan image and yellow image of each of the resultant samples was determined. Then, after the wedge-exposure of the sample 101 conducted in the same manner as that described above, it was processed in comparative developing steps described below, and the cyan density and yellow density were determined in the same manner as that described above. The density curve of the cyan image was compared with that of each sample (obtained at intervals of 10 seconds as described above), and the processing time in which the equal or higher cyan density was obtained is shown in Table 101.

The degree of lowering of the contrast of the yellow image was determined as follows: the yellow density of each sample (processed in the above-described comparative developing steps) was determined with such an exposure that yellow density of 2.5 would be obtained. The reduction in the density is also given in Table 101.

Comparative Color Developing Agent:

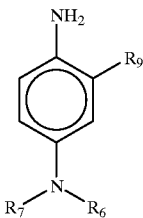

| Compound No. | $R_7$ | $R_8$ | $R_9$ | Remarks |
|---|---|---|---|---|
| COM-1 | $C_2H_5-$ | $-(CH_2)_3-OH$ | $-CH_3$ | GB Patent No. 807,899 Example 1 |
| COM-2 | $C_2H_5-$ | $-(CH_2)_4-OH$ | $-CH_3$ | GB Patent No. 807,899 Example 2 |
| COM-3 | $C_2H_5-$ | $-(CH_2)_6-OH$ | $-CH_3$ | GB Patent No. 807,899 Example 3 |
| COM-4 | $HO-(CH_2)_4-$ | $-(CH_2)_4-OH$ | $-CH_3$ | GB Patent No. 807,899 Example 5 |
| COM-5 | $HO-(CH_2)_3-$ | $-(CH_2)_3-OH$ | $-CH_3$ | GB Patent No. 807,899 Example 6 |
| COM-6 | $HO-(CH_2)_4-$ | $-(CH_2)_4-OH$ | $-H$ | GB Patent No. 807,899 Example 7 |
| COM-7 | $HO-(CH_2)_5-$ | $-(CH_2)_5-OH$ | $-H$ | GB Patent No. 807,899 Example 8 |
| COM-8 | $HO-(CH_2)_5-$ | $-(CH_2)_5-OH$ | $-OCH_3$ | GB Patent No. 807,899 Example 9 |
| COM-9 | $HO-(CH_2)_5-$ | $-(CH_2)_5-OH$ | $-OC_2H_5$ | Compound described in JP KOKAI No. Hei. 5-113635 |
| COM-10 | $C_2H_5-$ | $-(CH_2)_4-OH$ | $-OCH_3$ | Compound described in JP KOKAI No. Hei. 5-113635 |
| COM-11 | $C_2H_5-$ | $-(CH_2)_2-OH$ | $-OCH_3$ | Compound described in JP KOKAI No. Sho. 53-69035 |
| COM-12 | $C_4H_9-$ | $-CH_2CHCH_2OH$<br>$\quad\quad\quad\;\,\vert$<br>$\quad\quad\quad\;\,OH$ | $-OCH_3$ | Compound described in Journal fuer Signalaufzeichungsmaterialien Vol 2, P 277 (1974) |
| COM-13 | $HO-(CH_2)_4-$ | $-(CH_2)_5-OH$ | $-OCH_3$ | |
| COM-14 | $HO-(CH_2)_4-$ | $-(CH_2)_4-OH$ | $-OC_2H_5$ | |

Steps of Comparative Process:
(Processing Method):

| Step | Process time | Process temp. |
|---|---|---|
| Color development | 3 min 15 sec | 38° C. |
| Bleaching | 1 min 00 sec | 38° C. |
| Bleach-fixing | 3 min 15 sec | 38° C. |
| Washing with water (1) | 40 sec | 35° C. |
| Washing with water (2) | 1 min 00 sec | 35° C. |
| Stabilization | 40 sec | 38° C. |
| Drying | 1 min 15 sec | 55° C. |

The compositions of the processing liquids were as follows:

| (Color developer) | (unit: g) | |
|---|---|---|
| Diethylenetriaminepentaacetic acid | 1.0 | |
| 1-Hydroxyethylidene-1,1-diphosphonic acid | 2.0 | |
| Sodium sulfite | 4.0 | |
| Potassium carbonate | 30.0 | |
| Potassium bromide | 1.4 | |
| Potassium iodide | 1.5 | mg |
| Hydroxylamine sulfate | 2.4 | |
| N-[ethyl-N-(β-hydroxyethyl) amino]-2-methyl-aniline sulfate | 4.5 | |
| Water | ad 1.0 | l |
| pH (adjusted with potassium hydroxide and sulfuric acid) | 10.05 | |
| (Bleaching bath) | | |
| Ferric ammonium ethylenediaminetetraacetate dihydrate | 120.0 | |
| Disodium ethylenediaminetetraacetate | 10.0 | |
| Ammonium bromide | 100.0 | |
| Ammonium nitrate | 10.0 | |
| Bleaching accelerator (CH$_3$)$_2$N—CH$_2$—CH$_2$—S—S—CH$_2$—CH$_2$—N(CH$_3$)$_2$.2HCl | 0.005 | mol |
| Ammonia water (27%) | 15.0 | ml |
| Water | ad 1.0 | l |
| pH (adjusted with ammonia water and nitric acid) | 6.3 | |
| (Bleach-fixing bath) | | |
| Ferric ammonium ethylenediaminetetraacetate dihydrate | 50.0 | |
| Disodium ethylenediaminetetraacetate | 5.0 | |
| Sodium sulfite | 12.0 | |
| Aqueous ammonium thiosulfate solution (700 g/l) | 240.0 | ml |
| Ammonia water (27%) | 6.0 | ml |
| Water | ad 1.0 | l |
| pH (adjusted with ammonia water and acetic acid) | 7.2 | |

(Washing Water)

Tap water was passed through a mixed bed column packed with an H-type strongly acidic cation exchange resin (Amberlite IR-120B; a product of Rohm & Haas Co.) and an OH-type anion exchange resin (Amberlite IR-400; a product of Rohm & Haas Co.) to reduce calcium and magnesium ion concentration to 3 mg/l or below, and then 20 mg/l of sodium isocyanurate dichloride and 0.15 g/l of sodium sulfate were added to the water. pH of the water was in the range of 6.5 to 7.5.

| (Stabilizer) | (unit: g) |
|---|---|
| Sodium p-toluenesulfinate | 0.03 |
| Polyoxyethylene-p-mononylphenyl ether (average degree of polymerization: 10) | 0.2 |
| Disodium ethylenediaminetetraacetate | 0.05 |
| 1,2,4-Triazole | 1.3 |
| 1,4-Bis(1,2,4-triazol-1-ylmethyl)piperazine | 0.75 |
| Water | ad 1.0 l |
| pH | 8.5 |

TABLE 4

| Process | Color developing agent | Time | Difference in yellow density | Remarks |
|---|---|---|---|---|
| 151 | P-5 | 2 min. 10 sec. or more | — | Comp. Ex. |
| 152 | COM-1 | 2 min. 10 sec. | −0.03 | " |
| 153 | COM-2 | 2 min. | 0.06 | " |
| 154 | COM-3 | 2 min. 10 sec. or more | — | " |
| 155 | COM-4 | 2 min. 10 sec. | 0.05 | " |
| 156 | COM-5 | 2 min. 10 sec. or more | — | " |
| 157 | COM-6 | 2 min. 10 sec. or more | — | " |
| 158 | COM-7 | 2 min. 10 sec. or more | — | " |
| 159 | COM-8 | 1 min. 20 sec. | −0.72 | " |
| 160 | COM-9 | 1 min. 30 sec. | −0.81 | " |
| 161 | COM-10 | 1 min. 10 sec. | −0.78 | " |
| 162 | COM-11 | 1 min. 10 sec. | −0.65 | " |
| 163 | COM-12 | 1 min. 20 sec. | −0.76 | " |
| 164 | COM-13 | 1 min. 10 sec. | −0.52 | " |
| 165 | COM-14 | 1 min. 20 sec. | −0.55 | " |
| 166 | D-1 | 1 min. 10 sec. | −0.02 | Present invention |
| 167 | D-2 | 1 min. 10 sec. | −0.09 | " |
| 168 | D-3 | 1 min. 20 sec. | −0.01 | " |
| 169 | D-6 | 1 min. 30 sec. | −0.18 | " |
| 170 | D-7 | 1 min. 10 sec. | −0.03 | " |
| 171 | D-9 | 1 min. 30 sec. | −0.20 | " |
| 172 | D-11 | 1 min. 10 sec. | −0.08 | " |
| 173 | D-13 | 1 min. 20 sec. | −0.12 | " |
| 174 | D-15 | 1 min. 10 sec. | −0.16 | " |
| 175 | D-17 | 1 min. 10 sec. | −0.06 | " |
| 176 | D-19 | 1 min. 30 sec. | −0.16 | " |
| 177 | D-20 | 1 min. 20 sec. | −0.21 | " |
| 178 | D-21 | 1 min. 30 sec. | −0.14 | " |
| 179 | D-23 | 1 min. 30 sec. | −0.13 | " |
| 180 | D-25 | 1 min. 10 sec. | −0.07 | " |
| 181 | D-26 | 1 min. 10 sec. | −0.04 | " |
| 182 | D-27 | 1 min. 30 sec. | −0.25 | " |
| 183 | D-28 | 1 min. 10 sec. | −0.08 | " |
| 184 | D-30 | 1 min. 20 sec. | 0.02 | " |
| 185 | D-33 | 1 min. 30 sec. | −0.22 | " |
| 186 | D-36 | 1 min. 30 sec. | −0.26 | " |
| 187 | D-39 | 1 min. 30 sec. | −0.25 | " |
| 188 | D-42 | 1 min. 30 sec. | −0.26 | " |

In processes 157 and 158, the cyan densities of equal types were not obtained even after the development conducted for 2 minute 10 seconds.

It is apparent from Table 101 that the color developing agent of the present invention is capable of achieving the density in the red-sensitive layer within a far shorter development time than that necessitated by P-5 (process No. 151) and that the process was thus accelerated on a high level. The similar rapidity could be obtained with also compounds given in the Comparative Example, i.e. COM-8 (process 159), COM-9 (process 160), COM-10 (process 161), COM-11 (process 162), COM-12 (process 163), COM-13 (process 164) and COM-14 (process 165).

However, it is apparent that with the color developing agents used in the Comparative Example, the contrast of the yellow image is seriously lowered. On the contrary, it will be also apparent from, for example, the comparison of COM-8 (process 159) or COM-13 (process 164) with D-11 (process 172) or comparison of COM-12 (process 163) with D-30 (process 184), that with the color developing agents of the present invention, a desired gradation can be obtained in also the yellow image while the rapidity of the process is kept. Thus only a slight difference in the number of carbon atoms in the substituent of the p-phenylenediamine derivative causes a great difference in the effect.

It will be apparent from the comparison of COM-10 (process 161) or COM-11 (process 162) with D-19 (process 176) or COM-11 (process 172) that the problem of the lowering of the contract of the yellow image cannot be solved unless the color developing agent has two or more hydroxyl groups.

Both the acceleration of the process and the inhibition of the lowering of the contrast of the yellow image cannot be achieved at the same time unless the color developing agent of the present invention is used. It is impossible to infer this effect from the color developing agents used in the Comparative Example.

The staining with time (60° C., 70% RH, 5 days) after the process with the developing agent of the present invention was on only a low, acceptable level.

EXAMPLE 2

The same processing solution as that described in Example 2 of J.P. KOKAI Hei 5-53268 was prepared except that the color developing agent in the color developer for the color paper (sample B) was replaced with an equimolar amount of a color developing agent (D-1), (D-11) or (D-25) of the present invention, and the exposure and development were conducted. The development time could be reduced and the obtained yellow image had a desired gradation.

Thus, it is apparent that the color developing agent of the present invention is suitable for the rapid process, and a yellow image having a desired gradation can be obtained with it.

When the color developing agent of the present invention is used, the color development is accelerated and, in addition, the time necessitated for the steps of processing with a bath containing a bleaching solution or for the step wherein the last bath is used (such as step of washing with water) can be remarkably reduced.

Another advantage of the invention is that the processed photosensitive material can be prevented from staining, particularly staining with time after the process.

What is claimed is:

1. A p-phenylenediamine color developing agent represented by the following formula (D1) or (D2):

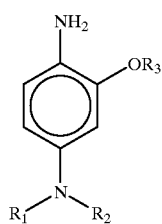
(D1)

wherein $R_1$ and $R_2$ each represent a hydroxyalkyl group having 2 or more carbon atoms, and $R_3$ represents an alkyl group, with the proviso that the sum of the carbon atoms in $R_1$, $R_2$ and $R_3$ is 9 or below, and

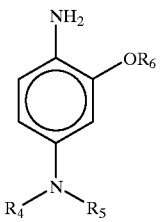
(D2)

wherein $R_4$ represents an alkyl group having 1 to 3 carbon atoms, $R_5$ represents an alkyl group having at least two hydroxyl groups, and $R_6$ represents an alkyl group having 1 to 4 carbon atoms.

2. The color developing agent of claim 1 wherein $R_1$ and $R_2$ each represent a hydroxyalkyl group having 2 to 6 carbon atoms, and $R_3$ represents an alkyl group having 1 to 5 carbon atoms with the proviso that the sum of the carbon atoms in $R_1$, $R_2$ and $R_3$ is 6 to 9.

3. The color developing agent of claim 2 wherein $R_3$ is methyl or ethyl group.

4. The color developing agent of claim 1 wherein $R_5$ represents an alkyl group having 2 to 3 hydroxyl groups and 3 to 9 carbon atoms.

5. The color developing agent of claim 4 wherein the sum of the carbon atoms in $R_4$, $R_5$ and $R_6$ is 5 to 10.

6. The color developing agent of claim 1 wherein $R_1$ and $R_2$ each represent a hydroxyalkyl group having 2 to 6 carbon atoms, and $R_3$ represents methyl or ethyl group with the proviso that the sum of the carbon atoms in $R_1$, $R_2$ and $R_3$ is 6 to 9, and $R_5$ represents an alkyl group having 2 to 3 hydroxyl groups and 3 to 9 carbon atoms with the proviso that the sum of the carbon atoms in $R_4$, $R_5$ and $R_6$ is 5 to 10.

7. A processing composition for silver halide color photographic materials, which comprises a p-phenylenediamine color developing agent represented by the following formula (D1) or (D2):

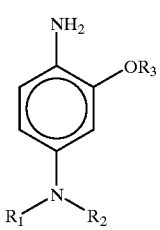
(D1)

wherein $R_1$ and $R_2$ each represent a hydroxyalkyl group having 2 or more carbon atoms, and $R_3$ represents an alkyl group, with the proviso that the sum of the carbon atoms in $R_1$, $R_2$ and $R_3$ is 9 or below, and

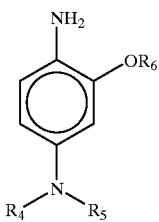 (D2)

wherein $R_4$ represents an alkyl group having 1 to 3 carbon atoms, $R_5$ represents an alkyl group having at least two hydroxyl groups, and $R_6$ represents an alkyl group having 1 to 4 carbon atoms, and balance of water, the pH of the composition being 9 to 12.5.

8. The processing composition of claim 7 wherein the p-phenylenediamine color developing agent is in an amount of 0.3 to 100 m mol per 1 liter of the processing composition.

9. The processing composition of claim 7 wherein $R_1$ and $R_2$ each represent a hydroxyalkyl group having 2 to 6 carbon atoms, and $R_3$ represents methyl or ethyl group with the proviso that the sum of the carbon atoms in $R_1$, $R_2$ and $R_3$ is 6 to 9, and $R_5$ represents an alkyl group having 2 to 3 hydroxyl groups and 3 to 9 carbon atoms with the proviso that the sum of the carbon atoms in $R_4$, $R_5$ and $R_6$ is 5 to 10.

* * * * *